US010960002B2

(12) United States Patent
Koo et al.

(10) Patent No.: US 10,960,002 B2
(45) Date of Patent: Mar. 30, 2021

(54) VOLATILE METABOLITE PROFILES FOR THE DIAGNOSIS AND TREATMENT OF MUCORALES FUNGI

(71) Applicant: The Brigham and Women's Hospital, Inc., Boston, MA (US)

(72) Inventors: Sophia Koo, Brookline, MA (US); Francisco Miguel Marty, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 315 days.

(21) Appl. No.: 16/301,100

(22) PCT Filed: May 15, 2017

(86) PCT No.: PCT/US2017/032651
§ 371 (c)(1),
(2) Date: Nov. 13, 2018

(87) PCT Pub. No.: WO2017/197386
PCT Pub. Date: Nov. 16, 2017

(65) Prior Publication Data
US 2019/0183887 A1   Jun. 20, 2019

Related U.S. Application Data

(60) Provisional application No. 62/335,841, filed on May 13, 2016.

(51) Int. Cl.
C07K 5/06 (2006.01)
C12Q 1/02 (2006.01)
(Continued)

(52) U.S. Cl.
CPC ........ *A61K 31/496* (2013.01); *A61K 31/4164* (2013.01); *A61K 38/12* (2013.01);
(Continued)

(58) Field of Classification Search
CPC ............ A61K 2300/00; A61K 31/4164; A61K 31/496; A61K 38/12; A61K 45/06;
(Continued)

(56) References Cited

U.S. PATENT DOCUMENTS 6,503,713 B1   1/2003   Rana
7,605,367 B2   10/2009  Miller et al.
(Continued)

FOREIGN PATENT DOCUMENTS

WO   WO 2014/039856   3/2014
WO   WO 2015/187938   10/2015
(Continued)

OTHER PUBLICATIONS

EP Extended European Search Report in European Appln. No. 177979020.9, dated Jan. 9, 2020, 8 pages.
(Continued)

*Primary Examiner* — Jennifer Wecker
(74) *Attorney, Agent, or Firm* — Fish & Richardson P.C.

(57) ABSTRACT

Methods for diagnosing, treating, and monitoring the treatment of mucormycosis are described. The methods can include detecting the presence of one or more volatile organic compounds (VOCs) in the breath of subjects suspected of having mucormycosis.

19 Claims, 35 Drawing Sheets

(51) Int. Cl.
| | |
|---|---|
| G01N 33/497 | (2006.01) |
| A61P 31/10 | (2006.01) |
| A61K 31/496 | (2006.01) |
| A61K 38/12 | (2006.01) |
| A61K 31/4164 | (2006.01) |
| C12Q 1/18 | (2006.01) |
| A61K 45/06 | (2006.01) |
| A61K 49/00 | (2006.01) |
| C12Q 1/04 | (2006.01) |
| A01N 37/46 | (2006.01) |

(52) U.S. Cl.
CPC ............. *A61K 45/06* (2013.01); *A61K 49/00* (2013.01); *A61K 49/0008* (2013.01); *A61P 31/10* (2018.01); *C12Q 1/025* (2013.01); *C12Q 1/04* (2013.01); *C12Q 1/18* (2013.01); *G01N 33/497* (2013.01); *G01N 2033/4975* (2013.01); *G01N 2033/4977* (2013.01); *G01N 2333/37* (2013.01)

(58) Field of Classification Search
CPC .. A61K 49/0008; A61K 49/00; A61K 8/0295; A61K 8/678; A61K 8/84; A61P 31/10; C12Q 1/025; C12Q 1/04; C12Q 1/18; G01N 2033/4975; G01N 2033/4977; G01N 2333/37; G01N 33/497; A61Q 19/00; A61Q 19/08; C07D 235/28; C07D 263/46; C07D 263/58; C07D 271/113; C07D 277/36; C07D 277/56; C07D 277/587; C07D 285/125; Y02P 20/55
See application file for complete search history.

(56) References Cited

U.S. PATENT DOCUMENTS

| | | | |
|---|---|---|---|
| 2007/0003996 | A1 | 1/2007 | Hitt et al. |
| 2009/0078865 | A1 | 3/2009 | Zapata et al. |
| 2010/0129434 | A1 | 5/2010 | Ibrahim et al. |
| 2010/0291617 | A1 | 11/2010 | Trevejo |
| 2013/0108642 | A1 | 5/2013 | Ibrahim et al. |
| 2013/0168548 | A1 | 7/2013 | Li et al. |
| 2013/0260395 | A1 | 10/2013 | Luppi et al. |
| 2015/0233895 | A1 | 8/2015 | Koo et al. |

FOREIGN PATENT DOCUMENTS

| | | |
|---|---|---|
| WO | WO 2016/019371 | 2/2016 |
| WO | WO 2018/071519 | 4/2018 |

OTHER PUBLICATIONS

Jantan et al., "Correlation Between Chemical Composition and Antifungal Activity of the Essential Oils of Eight *Cinnamomum* Species," Pharmaceutical Biology, Jan. 2008, 46(6):406-412.
Koo et al., "A Breath Fungal Secondary Metabolite Signature to Diagnose Invasive Aspergillosis," Clinical Infectious Diseases, Dec. 2014, 59(12):1733-1740.
Scotter et al., "Real-time detection of common microbial volatile organic compounds from medically important fungi by Selected Ion Flow Tube-Mass Spectrome try (SIFT-MS)" Journal of Microbiological Methods, Nov. 2005, 63(2):127-134.
Baddley et al., "Patterns of susceptibility of Aspergillus isolates recovered from patients enrolled in the Transplant-Associated Infection Surveillance Network." J. Clin. Microbiol., 2009, 47(10):3271-3275.
Bernal-Martinez et al, "Development of a single tube multiplex real-time PCR to detect the most clinically relevant *Mucormycetes* species," Clin. Microbiol. Infect., Aug. 2013, 19(1):E1-7.
Chambers et al, "Developments in novel breath tests for bacterial and fungal pulmonary infection," Current Opinion in Pulmonary Medicine, May 2012, 18(3):228-232.
Czarnik, "Encoding strategies in combinatorial chemistry," Curr. Opin. Chem. Bio., Jun. 1997, 1(1):60-66.
Davis et al, "Spore biomarker detection using a MEMS differential mobility spectrometer," Transducers'03, 12th International Conference on Solid-State Sensors, Actuators and Microsystems. Digest of Technical Papers, 2003, (2):1233-1238.
Emedicine.medscape.com [online] McDonald et al "Mucormycosis (Zygomycosis)," Sep. 10, 2018, [retrieved on Sep. 25, 2019], retrieved from: URL <emedicine.medscape.com/article/222551>.
Fong et al, "Automated Peak Detection and Matching Algorithm for Gas Chromatography—Differential Mobility Spectrometry," Anal. Chem., Mar. 2011, 83:1537-1546.
Kanu et al, "Ion mobility spectrometry detection for gas chromatography," J. Chromatography A, Nov. 2007, 1177(1):12-27.
Kanu et al, "Ion mobility-mass spectrometry," J. Mass. Spectrom., Jan. 2008, 43(1):1-22.
Kolakowski et al, "Review of applications of high-field asymmetric waveform ion mobility spectrometry (FAIMS) and differential mobility spectrometry (DMS)," The Analyst, Jun. 2007, 132(9):842-864.
Krebs et al, "Detection of biological and chemical agents using Differential Mobility Spectrometry (DMS) technology," IEEE Sensors Journal, Aug. 2005, 5(4):696-702.
Luong et al, "Gas chromatography with state-of-the-art micromachined differential mobility detection: operation and industrial applications," J. Chromatogr. Sci., May 2006, 44(5):276-286.
Miller et al, "A MEMS Radio-Frequency Ion Mobility Spectrometer for Chemical Agent Detection," Seanors and Actuators A Physical, Jul. 2001, (91):307-318.
Millon et al, "Quantitative polymerase chain reaction detection of circulating DNA in serum for early diagnosis of mucormycosis in immunocompromised patients," Clin. Infect. Dis., May 2013, 56(10):e95-101.
Milroy et al. "Aspergillosis of the nose and paranasal sinuses," J. Clin. Pathol., Feb. 1989, 42(2):123-127.
Nazarov et al, "Pressure effects in differential mobility spectrometry," Anal. Chem., Nov. 2006, 78(22):7697-7706.
PCT International Preliminary Report on Patentability in PCT Aplln. No. PCT/US2017/32651, dated Nov. 13, 2018, 8 pages.
PCT International Search Report in PCT Aplln. No. PCT/US2017/32651, dated Aug. 25, 2017, 3 pages.
Shnayderman et al, "Species-specific bacteria identification using differential mobility spectrometry and bioinformatics pattern recognition," Anal. Chem., Sep. 2005, 77(18):5930-5937.
Spellberg and Ibrahim, "Recent advances in the treatment of mucormycosis." Curr Infect Dis Rep. Nov. 12, 2010(6):423-9.
Spellberg et al., "Recent advances in the management of mucormycosis: from bench to bedside," Clin. Infect. Dis., Jun. 2009, 48(12):1743-1751.
UpToDate.com, Kauffman et al, "Treatment and prevention of invasive aspergillosis," https://www.uptodate.com/contents/treatment-and-prevention-of-invasive-aspergillosis.
Walsh et al, "Treatment of Aspergillosis: Clinical Practice Guidelines of the Infectious Diseases Society of America," Clinical Infectious Diseases, 2008, 46:327-360.
Wihlborg et al, "Headspace sorptive extraction and GC-TOFMS for the identification of volatile fungal metabolites," Journal of Microbiological Methods, Jun. 2008, 75(2):244-250.

Cedrene 2H-3,9a-Methano-1-benzoxepin, octahydro-2,2,5a,9-tetramethyl-, [3R-(3α,5aα,9α,9aα)]-

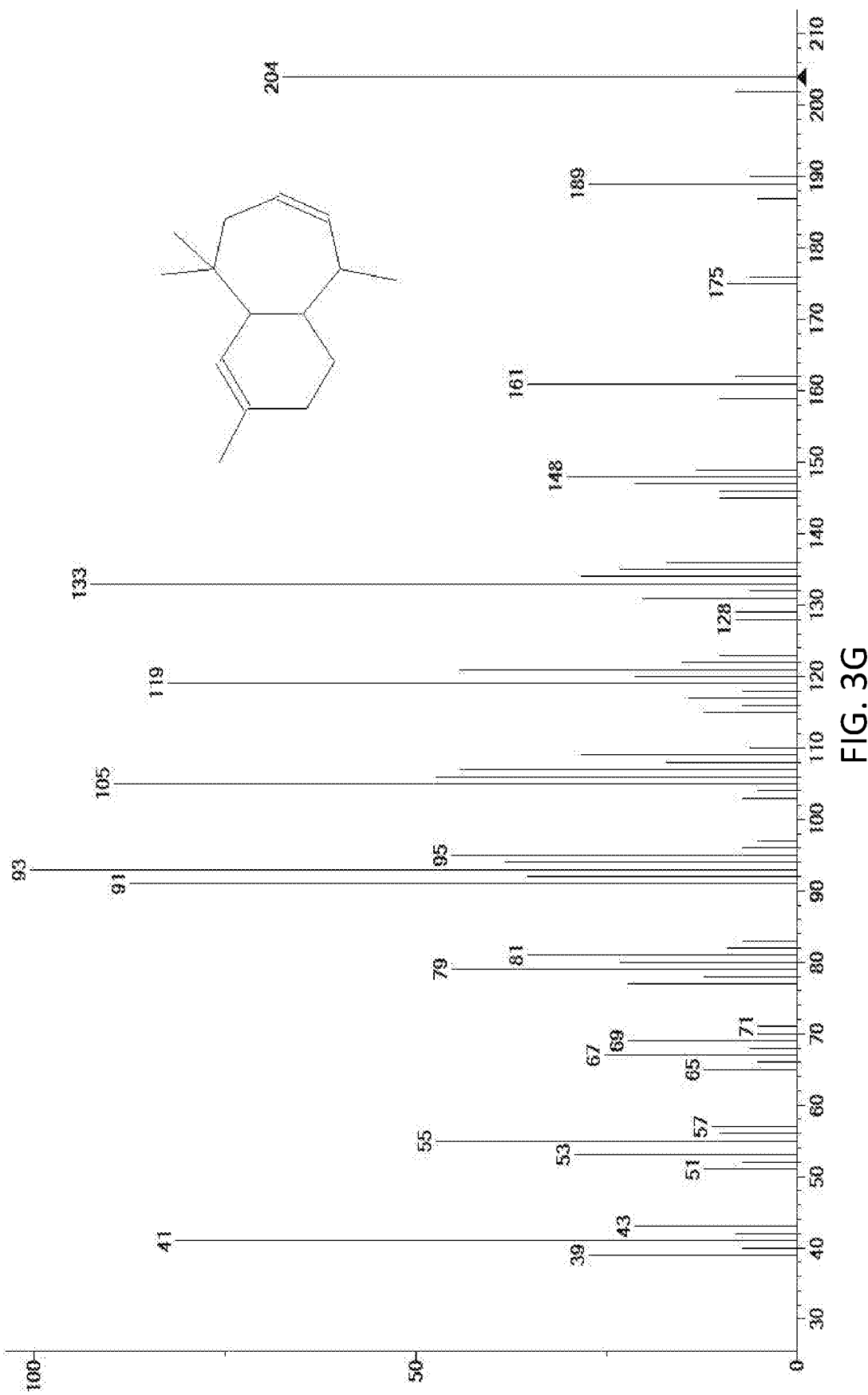
FIG. 3G cis-(-)2,4a,5,6,9a-Hexahydro-3,5,5,9-tetramethyl(1H)benzocycloheptene

VOLATILE METABOLITE PROFILES FOR THE DIAGNOSIS AND TREATMENT OF MUCORALES FUNGI

CLAIM OF PRIORITY

This application is a § 371 National Stage Application of PCT/US2017/032651, filed May 15, 2017, which claims the benefit of U.S. Provisional Application No. 62/335,841 filed May 13, 2016. The entire contents of the foregoing are incorporated herein by reference.

FEDERALLY SPONSORED RESEARCH OR DEVELOPMENT

This invention was made with Government support under Grant No. AI097225 awarded by the National Institutes of Health. The Government has certain rights in the invention.

TECHNICAL FIELD

Provided herein are methods for diagnosing, treating, and monitoring the treatment of mucormycosis. The methods can include detecting the presence of one or more volatile organic compounds (VOCs) in the breath of subjects suspected of having mucormycosis.

BACKGROUND

Members of the fungal order Mucorales cause life-threatening, rapidly progressive infections in immunocompromised patients, especially in patients with diabetes mellitus, chemotherapy-induced neutropenia, or transplant recipients who are immunosuppressed as a result of receiving glucocorticoid treatment for graft-versus-host disease (GVHD). The diagnosis of mucormycosis is exceedingly challenging, requiring a biopsy for diagnosis, and distinguishing mucormycosis from aspergillosis based on clinical features is extremely difficult. Because of the fulminant nature of these infections and the lack of noninvasive diagnostics for this infection, mortality rates remain high, at 50-90%. Timely diagnosis with prompt initiation of appropriate antifungal therapy directed against mucormycosis improves clinical outcomes.

SUMMARY

As described herein, the present inventors have identified unique, species-specific profiles of volatile organic compounds (VOCs) produced by pathogenic Mucorales species, and other pathogenic fungi in vitro that can be used to distinguish pathogenic fungal species from each other, and to monitor the efficacy of treatments.

Thus, provided herein are methods for diagnosing a subject with mucormycosis. The methods include obtaining a sample comprising breath of a subject or suspected of comprising a Mucorales species fungi isolated from a subject; detecting the presence in the sample of volatile organic compounds (VOCs) produced by the Mucorales species in a sample comprising breath from the subject or headspace from a culture suspected of comprising Mucorales isolated from the subject, wherein the VOCs are cedrene 8,14-, cedrene, and 1H-Indene, 2,3,3a,4-tetrahydro-3,3a,6-trimethyl-1-(1-methylethyl)-; and diagnosing a subject as having mucormycosis when the VOCs are present in the sample.

In some embodiments, the methods include detecting the presence in a sample comprising headspace from a culture of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene, wherein:

the presence of one, two, three or more of 1H-Indene, 2,3,3a,4-tetrahydro-3,3a,6-trimethyl-1-(1-methylethyl)-, longipinene, cedrene, aromandendrene, alloaromadendrene, cubebol, and aciphyllene indicates a diagnosis of *Rhizopus arrhizus* var. *arrhizus*;

the presence of one, two, three or more of 1H-Indene, 2,3,3a,4-tetrahydro-3,3a,6-trimethyl-1-(1-methylethyl)-, isoledene, daucene, isocomene, isocaryophyllene, humulene, and isodaucene indicates a diagnosis of *Rhizopus arrhizus* var. *delemar*; and/or the presence of one, two, three or more of alloaromadendrene, cubebene, cyperene, and α-bisabolene indicates a diagnosis of *Rhizopus microsporus*.

In some embodiments, the methods include detecting the presence, in a sample breath from a subject suspected of being infected with Mucorales fungi, a level of one, two, three, four or more of Cedrene; cedranoxide, 8, 14-; 1H-Indene,2,3,3a,4-tetrahydro-3,3a,6-trimethyl-1-(1-methylethyl)-; Longifolene; 2H-3,9a-Methano-1-benzoxepin; octahydro-2,2,5a,9-tetramethyl-, [3R-(3α,5aα,9α,9aα)]-; cis-(−) 2,4a,5,6,9a-Hexahydro-3,5,5,9-tetramethyl(1H) benzocycloheptene; selina-5,11-diene; or α-guaiene; alloaromadendrene, wherein:

the presence of one, two, three, or more of longifolene; 2H-3,9a-Methano-1-benzoxepin; octahydro-2,2,5a,9-tetramethyl-, [3R-(3α,5aα,9α,9aα)]-; and cis-(−)2,4a,5,6,9a-Hexahydro-3,5,5,9-tetramethyl(1H)benzocycloheptene indicates the presence of *Rhizopus arrhizus* var. *arrhizus*;

the presence of one, two, or all three of cedrene; selina-5,11-diene; and cedranoxide, 8, 14- indicates the presence of *Rhizopus microsporus*; and the presence of □-guaiene and alloaromadendrene indicates the presence of *Rhizopus arrhizus* var. *delemar*.

In some embodiments, the methods include detecting the presence in a sample comprising breath from a subject suspected of being infected with Mucorales fungi, the presence of one, two, or all three of cedrene; cedranoxide, 8, 14-; and 1H-Indene, 2,3,3a,4-tetrahydro-3,3a,6-trimethyl-1-(1-methylethyl)-, and diagnosing the patient with a Mucorales fungal infection.

In some embodiments, the methods include detecting the presence of one, two, three, or all four of 1H-Indene, 2,3,3a,4-tetrahydro-3,3a,6-trimethyl-1-(1-methylethyl)-; cedrene; selina-5,11-diene, and cedranoxide, 8,14-, and diagnosing the patient with a Mucorales fungal infection.

In some embodiments, the Mucorales fungal infection is an infection with a *Rhizopus* species fungus.

In some embodiments, the methods include selecting and optionally administering an antifungal treatment for mucormycosis to a subject, wherein one, two, three, or more of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene was detected in the headspace from a culture from the subject.

In some embodiments, the methods include selecting and optionally administering an antifungal treatment for mucormycosis to a subject who has cedrene; cedranoxide, 8, 14-; and 1H-Indene, 2,3,3a,4-tetrahydro-3,3a,6-trimethyl-1-(1-methylethyl)- in their breath.

In some embodiments, the treatment comprises administration of one or more doses of one or more antifungal compounds as described herein.

Also provided herein are methods for monitoring efficacy of a treatment for mucormycosis in a subject. The methods include determining a first level of one, two, three, or more volatile organic compounds (VOCs) produced by a mucormycosis species in a sample comprising breath from the subject or headspace from a culture suspected of comprising Mucorales fungi isolated from the subject, wherein the VOCs are cedrene 8,14-, cedrene, and 1H-Indene, 2,3, 3a,4-tetrahydro-3,3a,6-trimethyl-1-(1-methylethyl)-, and optionally cedranoxide 8-14-, in the subject;

administering a treatment for mucormycosis to the subject; determining a second level of the VOCs in a sample obtained after administration of the treatment to the subject; and comparing the first and second levels of VOCs, wherein a decrease in the VOCs indicates that the treatment has been effective in treating the mucormycosis in the subject, and an increase or no change indicates that the treatment has not been effective in treating the mucormycosis in the subject.

In some embodiments, the treatment include administration of one or more doses of one or more antifungal compounds.

Also provided herein are methods for identifying a candidate compound for the treatment of mucormycosis. In some embodiments, the methods include providing a test culture comprising one or more Mucorales species; detecting a baseline level of fungal VOCs in the headspace of the culture in the absence of the test compound, wherein the VOCs are cedrene 8,14- and 1H-Indene, 2,3,3a,4-tetrahydro-3,3a,6-trimethyl-1-(1-methylethyl)-, and optionally cedranoxide 8-14-, in the subject; contacting the test culture with a test compound; determining a second level of the VOCs in a test culture; comparing the second level of VOCs to the baseline level; and identifying a test compound that decreases levels of fungal VOCs in the test culture as a candidate compound for the treatment of mucormycosis.

Further, provided herein are methods for detecting the presence of a mucormycosis infection in a culture. In some embodiments, the methods include obtaining a sample comprising gas from the headspace of the culture; determining the presence of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene, wherein:

the presence of one, two, three or more of 1H-Indene, 2,3,3a,4-tetrahydro-3,3a,6-trimethyl-1-(1-methylethyl)-, longipinene, cedrene, aromandendrene, alloaromadendrene, cubebol, and aciphyllene indicates the presence of *Rhizopus arrhizus* var. *arrhizus* in the culture;

the presence of one, two, three or more of 1H-Indene, 2,3,3a,4-tetrahydro-3,3a,6-trimethyl-1-(1-methylethyl)-, isoledene, daucene, isocomene, isocaryophyllene, humulene, and isodaucene indicates the presence of *Rhizopus arrhizus* var. *delemar* in the culture; and the presence of one, two, three or more of alloaromadendrene, cubebene, cyperene, and α-bisabolene indicates the presence of *Rhizopus microsporus* in the culture.

In some embodiments of the various methods described herein, determining the presence of a VOC includes assaying the sample to detect the presence the VOC.

In some embodiments of the various methods described herein, assaying the sample to detect the presence the VOC includes using a gas chromatography (GC) or spectrometry method.

In some embodiments of the various methods described herein, the spectrophotometry method is mobility spectrometry (IMS) or differential mobility spectrometry (DMS).

In some embodiments of the various methods described herein, the subject is a human.

In some embodiments of the various methods described herein, the antifungal compound is an amphotericin B formulation; an azole antifungal compound; or an echinocandin antifungal compound.

In some embodiments of the various methods described herein, determining the presence of a VOC comprises assaying the sample to detect the presence the VOC. In some embodiments, assaying the sample to detect the presence the VOC comprises using a gas chromatography (GC) or spectrometry method. In some embodiments, the spectrophotometry method is mobility spectrometry (IMS) or differential mobility spectrometry (DMS).

In some embodiments of the various methods described herein, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety, including especially WO 2014/039856 and WO 2015/187938. In case of conflict, the present specification, including definitions, will control.

Other features and advantages of the invention will be apparent from the following detailed description and figures, and from the claims.

DESCRIPTION OF DRAWINGS

FIG. 1O. MS electron ionization fragmentation pattern for isodaucene, *Rhizopus arrhizus* var. *delemar*.

DETAILED DESCRIPTION

Figure 1A:
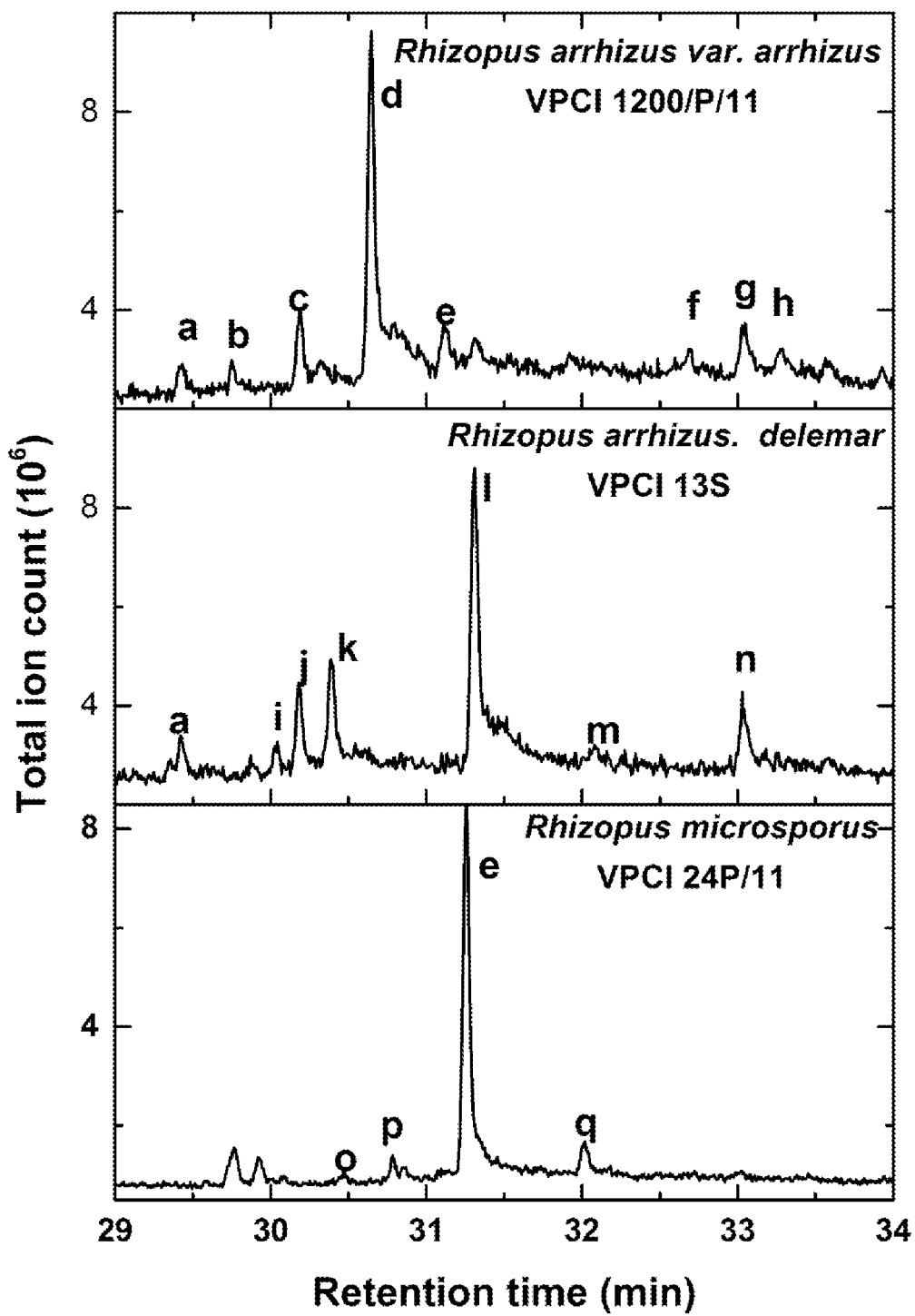
FIG. 1A. GC-MS total ion chromatograms of headspace gas from cultures of *Rhizopus arrhizus* var. *arrhizus*, *Rhizopus arrhizus* var. *delemar*, and *Rhizopus microsporus*; (a) 1H-Indene, 2,3,3a,4-tetrahydro-3,3a,6-trimethyl-1-(1-methylethyl)- (b) Longipinene (c) Cedrene (d) Aromandendrene (e) Alloaromadendrene (f) Cubebol (g) Aciphyllene (h) Dauca-4(11),8-diene (i) Isoledene (j) Daucene (k) Isocomene (l) Isocaryophyllene (m) Humulene (n) Isodaucene (o) Cubebene (p) Cyperene (q) α-Bisabolene; MS fragmentations below.
Figure 1B:
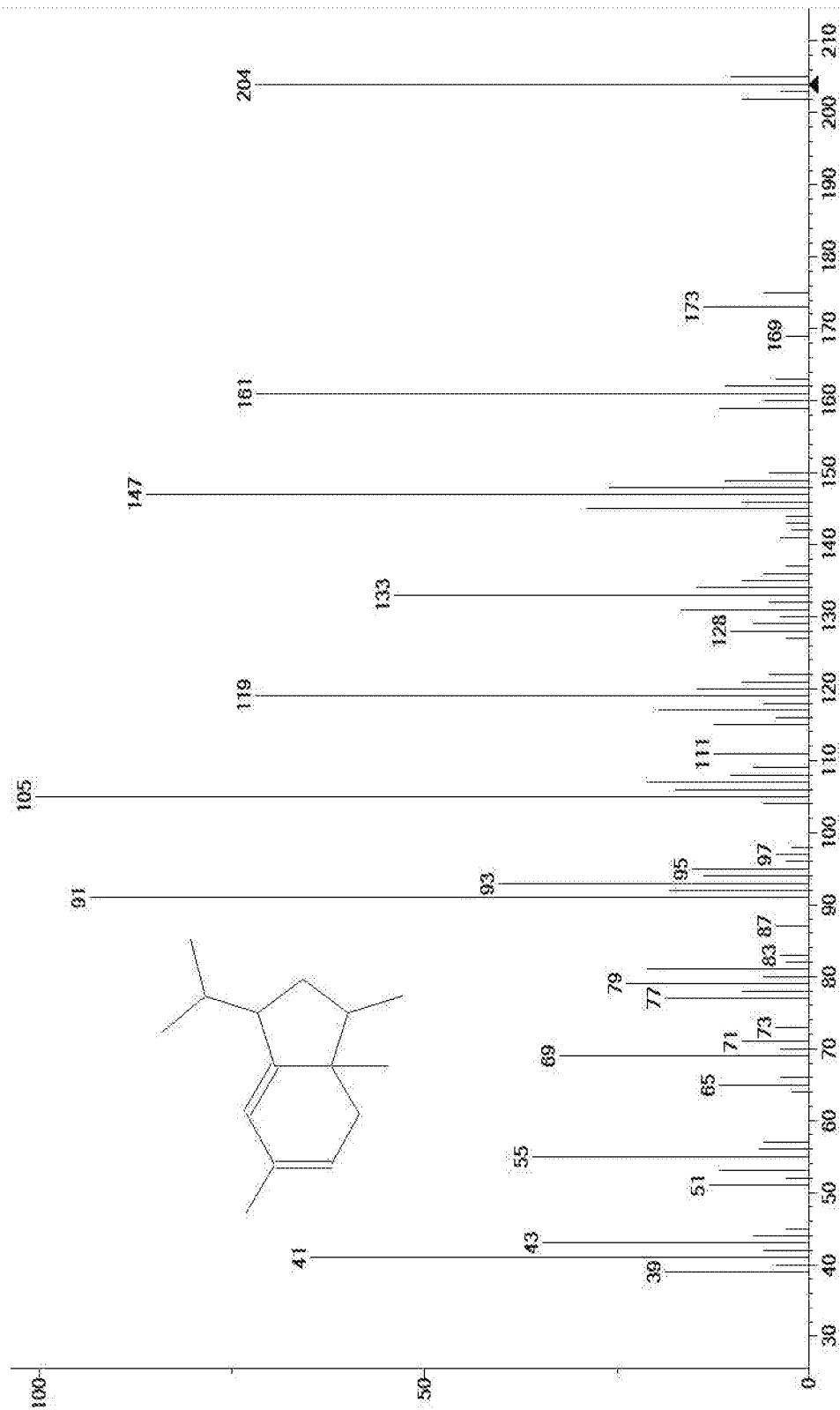
FIG. 1B. MS electron ionization fragmentation pattern for 1H-Indene, 2,3,3a,4-tetrahydro-3,3a,6-trimethyl-1-(1-methylethyl)-, present in cultures of *Rhizopus arrhizus* var. *arrhizus* and *Rhizopus arrhizus* var. *delemar*.
Figure 1C:
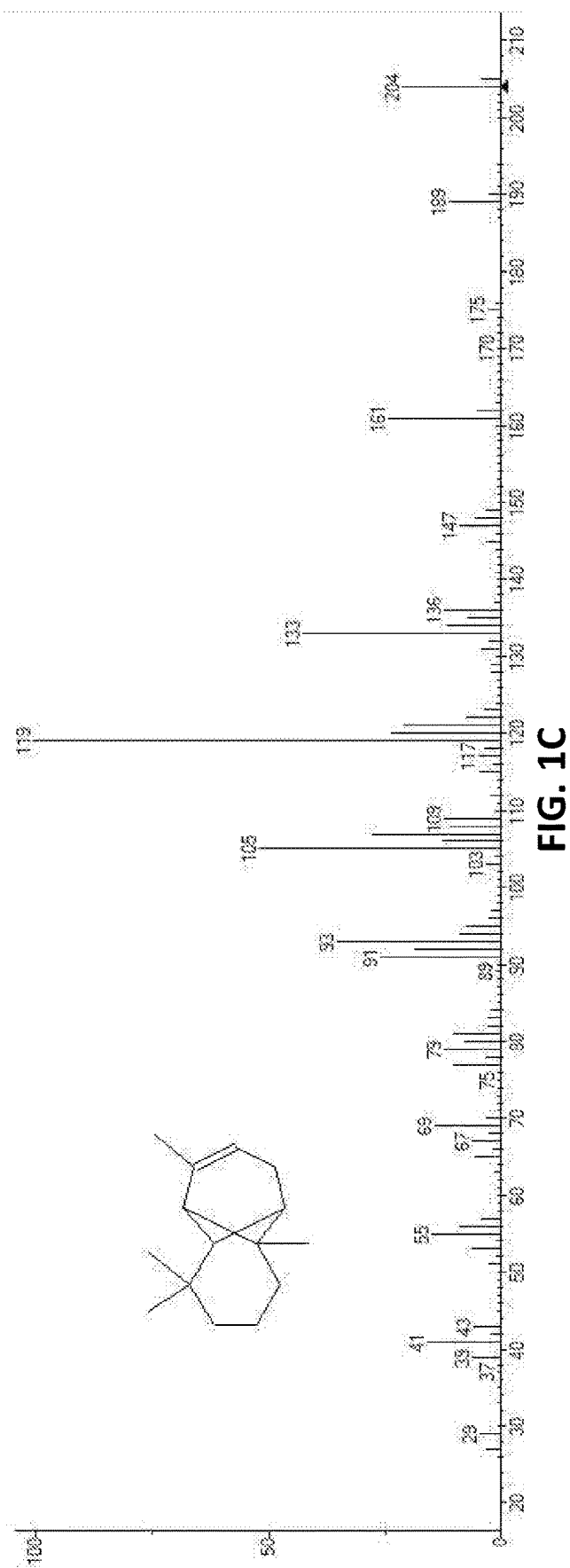
FIG. 1C. MS electron ionization fragmentation pattern for longipinene, *Rhizopus arrhizus* var. *arrhizus*.
Figure 1D:
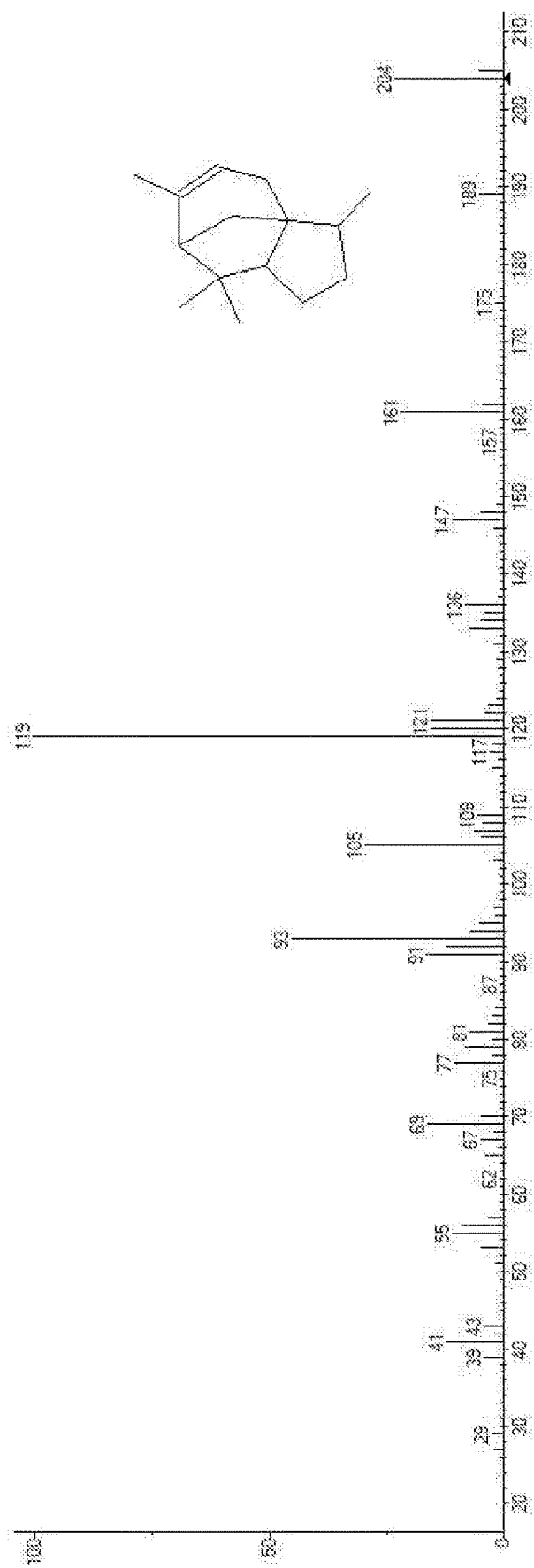
FIG. 1D. MS electron ionization fragmentation pattern for cedrene, *Rhizopus arrhizus* var. *arrhizus*.
Figure 1E:
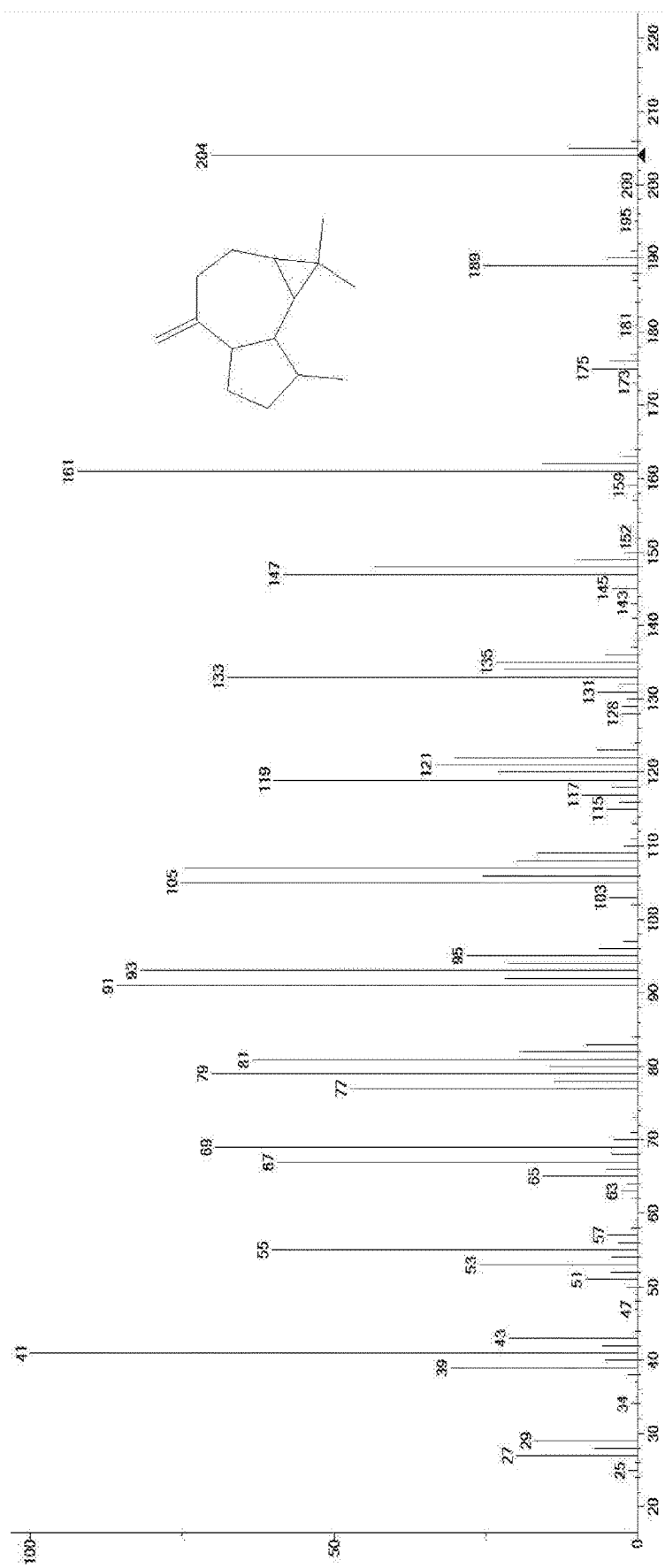
FIG. 1E. MS electron ionization fragmentation pattern for aromandendrene, *Rhizopus arrhizus* var. *arrhizus*.
Figure 1F:
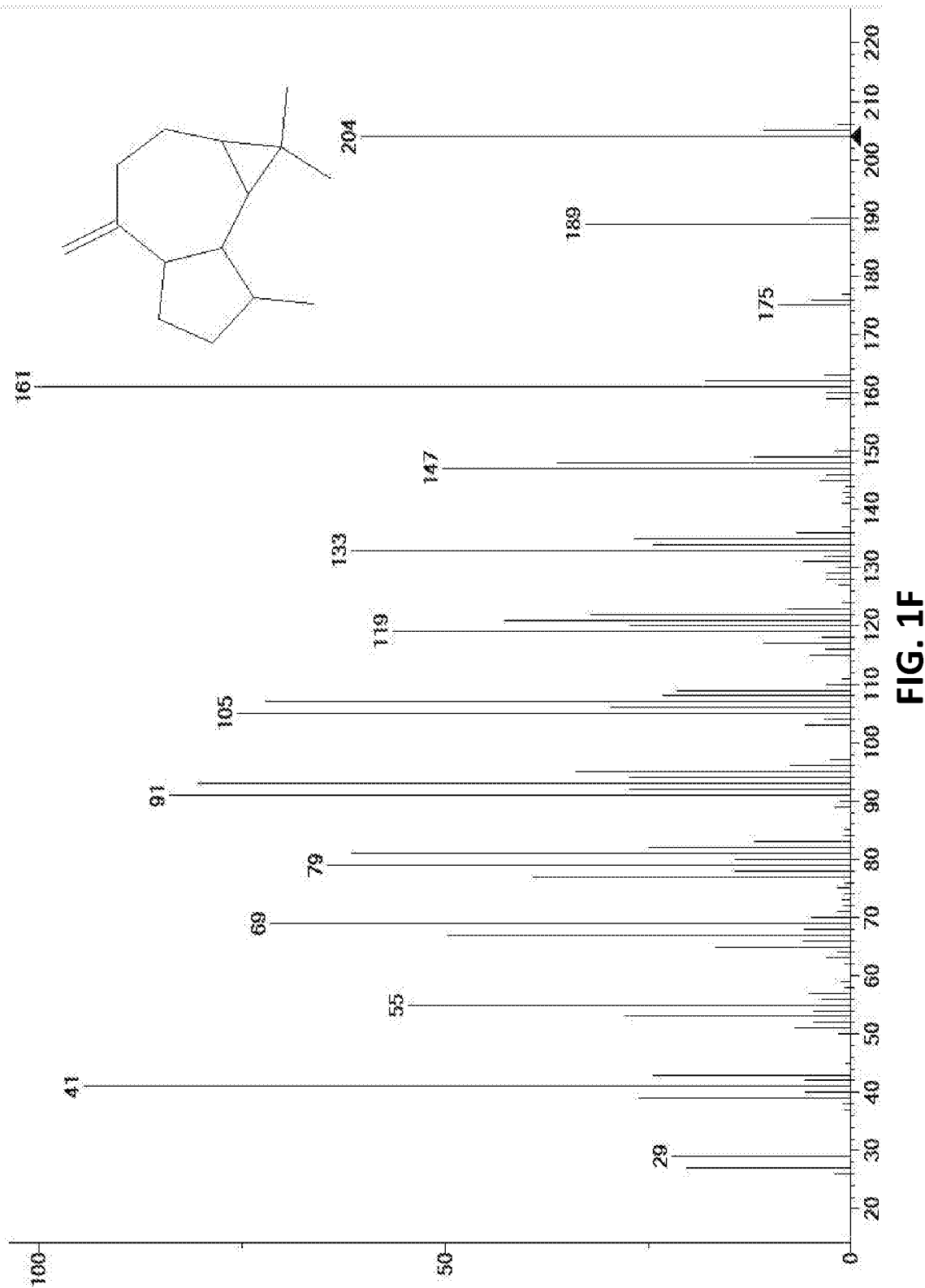
FIG. 1F. MS electron ionization fragmentation pattern for alloaromadendrene, *Rhizopus arrhizus* var. *arrhizus*.
Figure 1G:
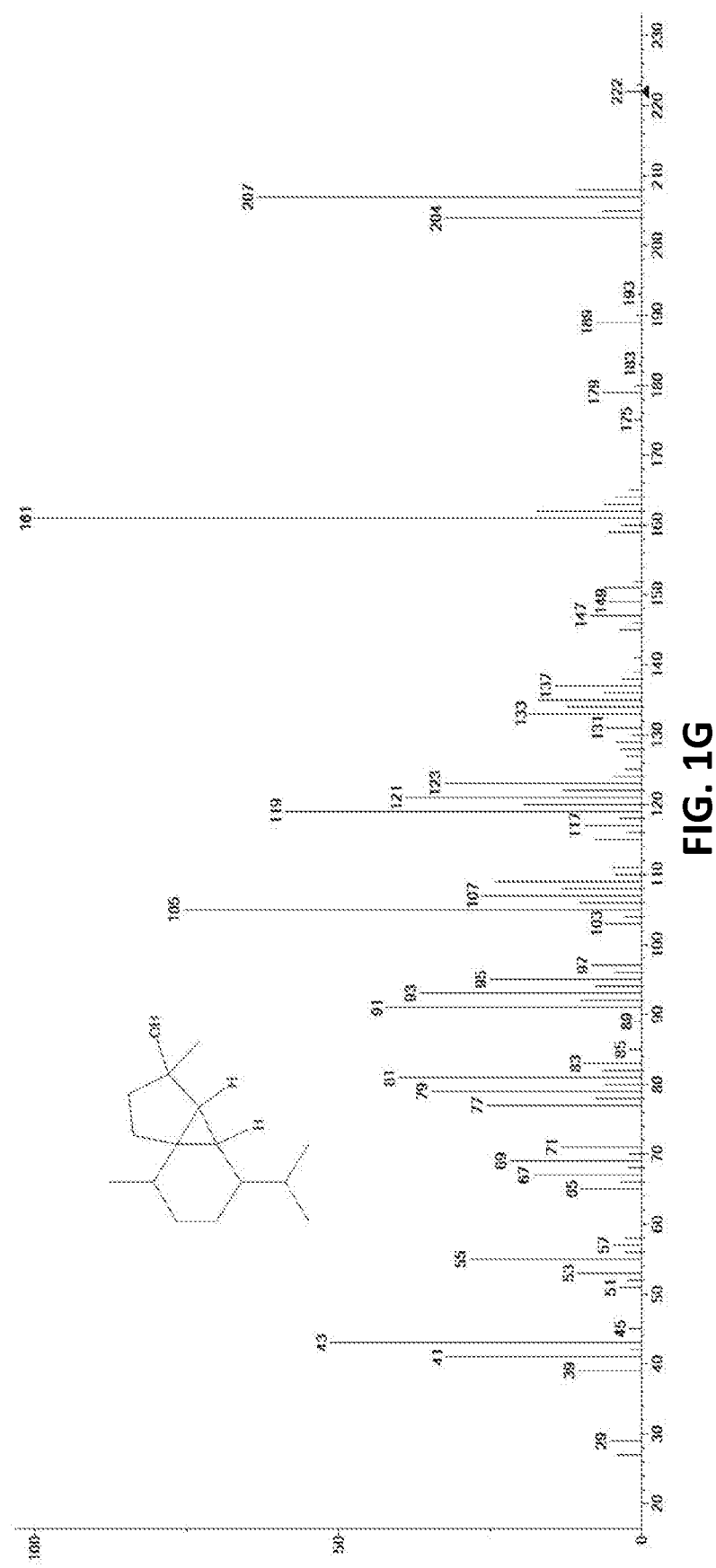
FIG. 1G. MS electron ionization fragmentation pattern for cubebol, *Rhizopus arrhizus* var. *arrhizus*.
Figure 1H:
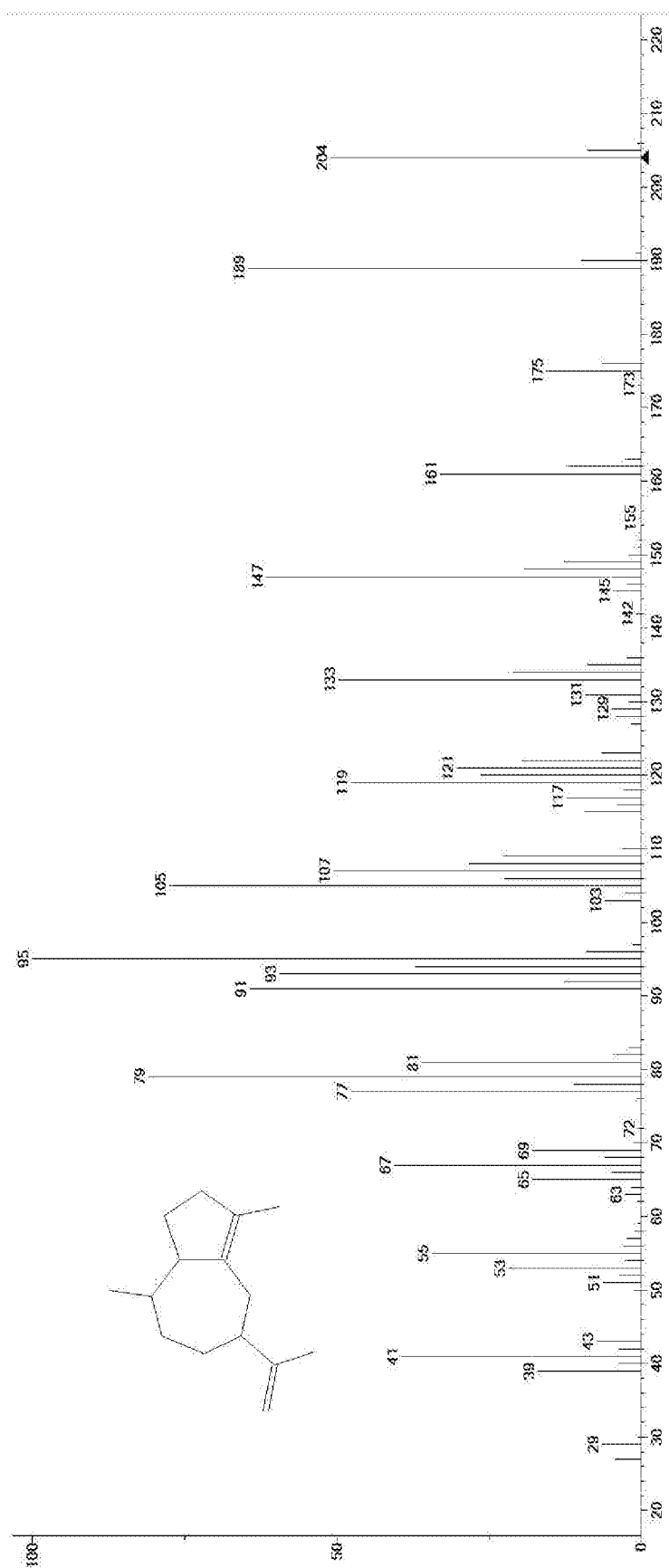
FIG. 1H. MS electron ionization fragmentation pattern for aciphyllene, *Rhizopus arrhizus* var. *arrhizus*.
Figure 1I:
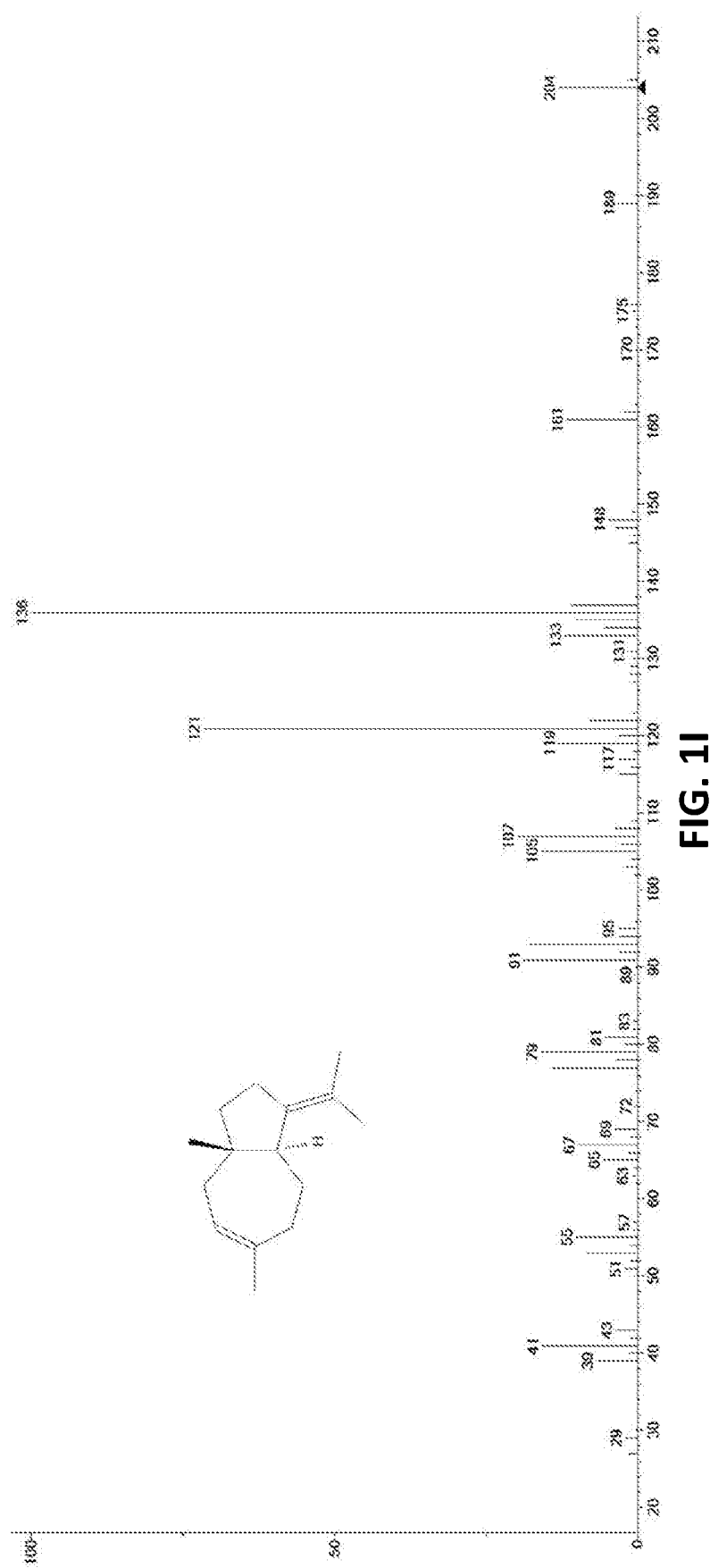
FIG. 1I. MS electron ionization fragmentation pattern for dauca-4(11),8-diene, *Rhizopus arrhizus* var. *arrhizus*.
Figure 1J:
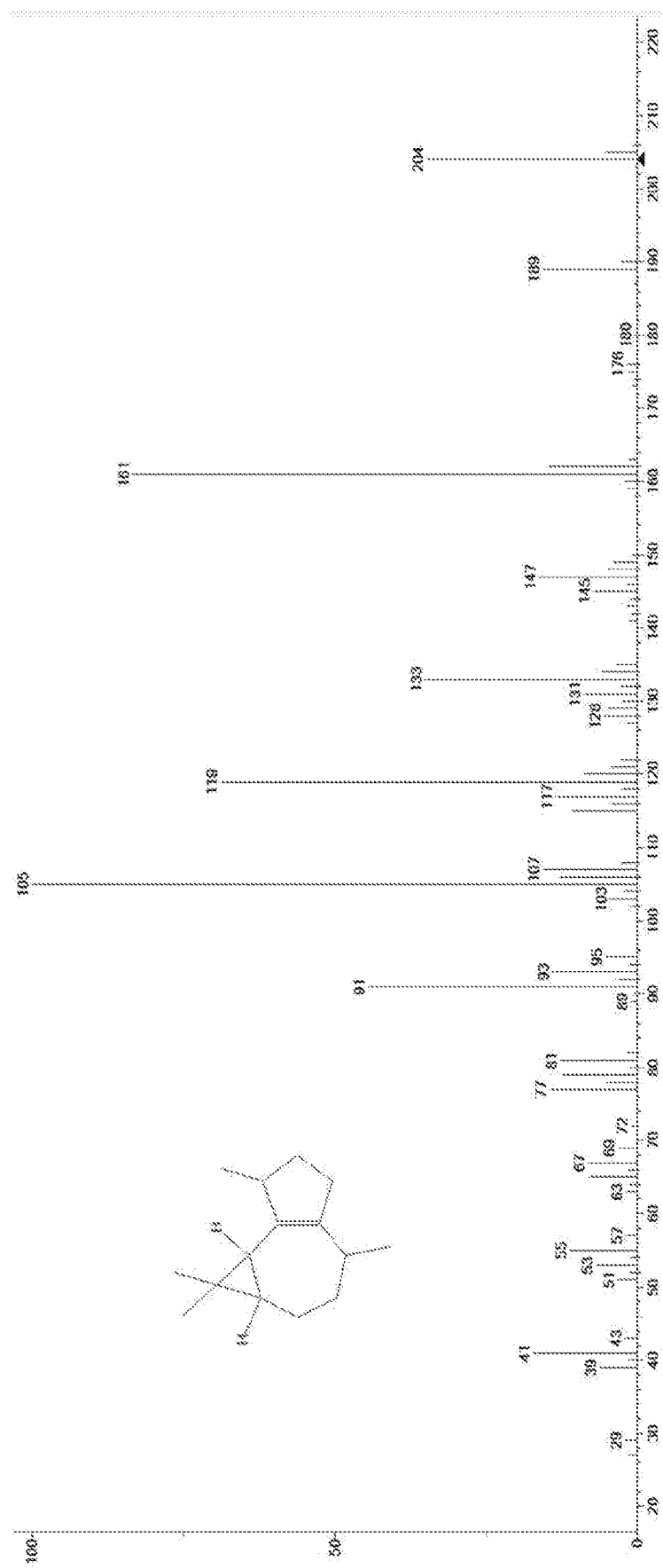
FIG. 1J. MS electron ionization fragmentation pattern for isoledene, *Rhizopus arrhizus* var. *delemar*.
Figure 1K:
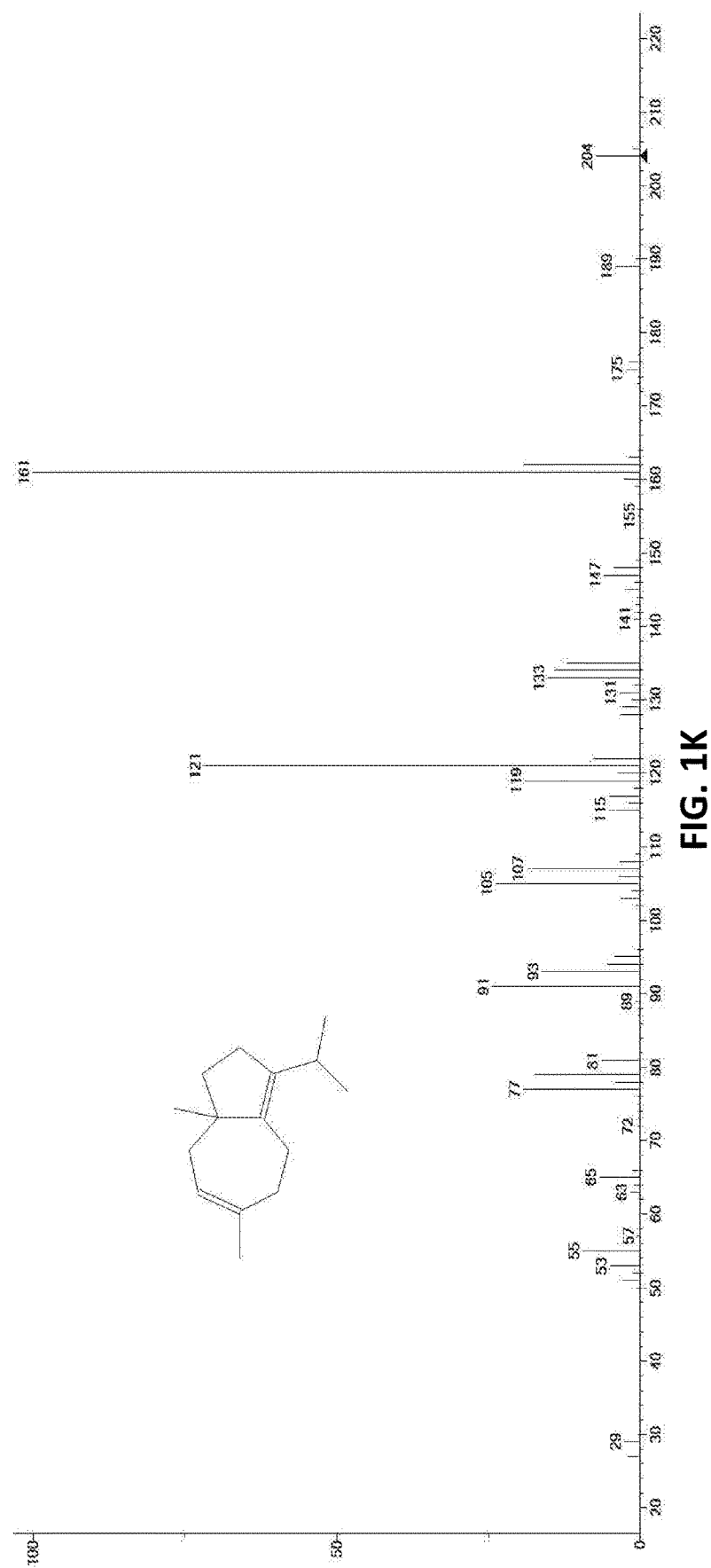
FIG. 1K. MS electron ionization fragmentation pattern for daucene, *Rhizopus arrhizus* var. *delemar*.
Figure 1L:
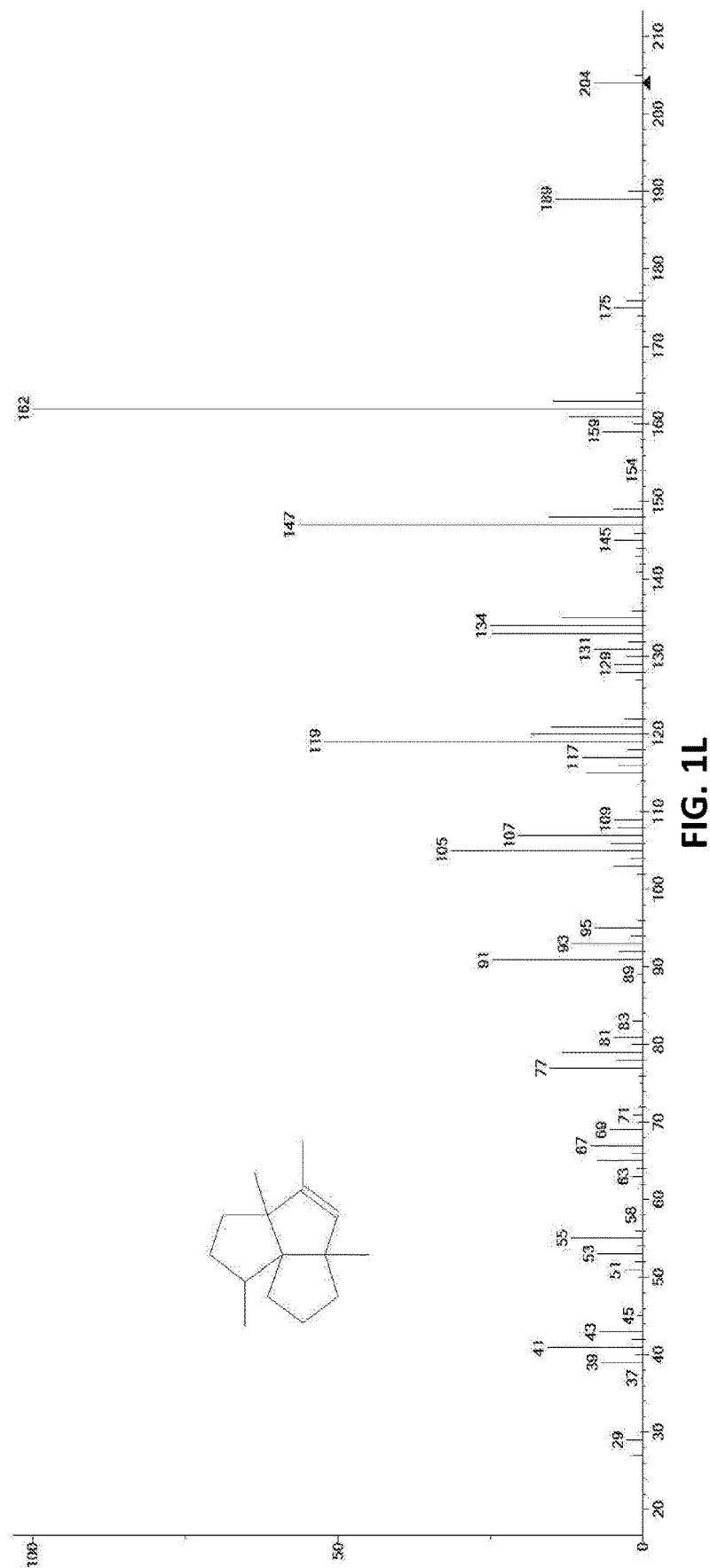
FIG. 1L. MS electron ionization fragmentation pattern for isocomene, *Rhizopus arrhizus* var. *delemar*.
Figure 1M:
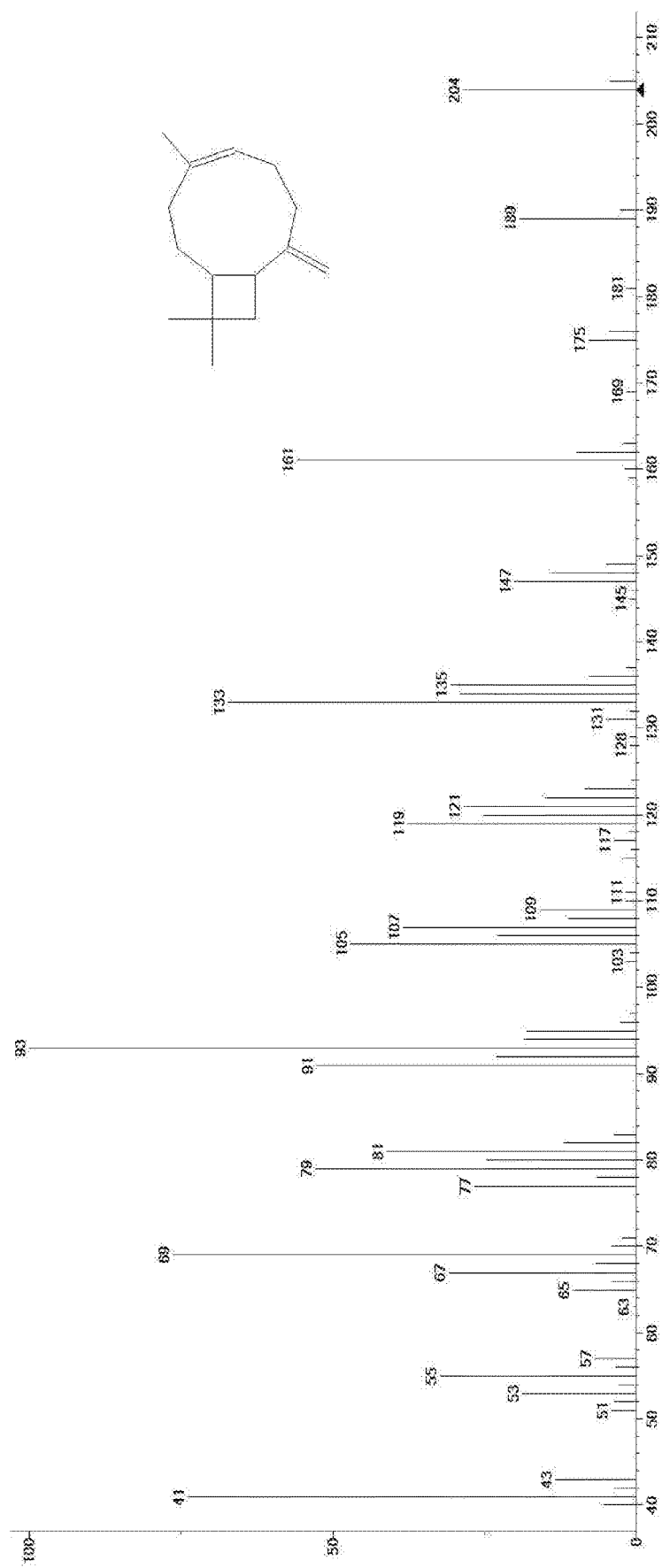
FIG. 1M. MS electron ionization fragmentation pattern for isocaryophyllene, *Rhizopus arrhizus* var. *delemar*.
Figure 1N:
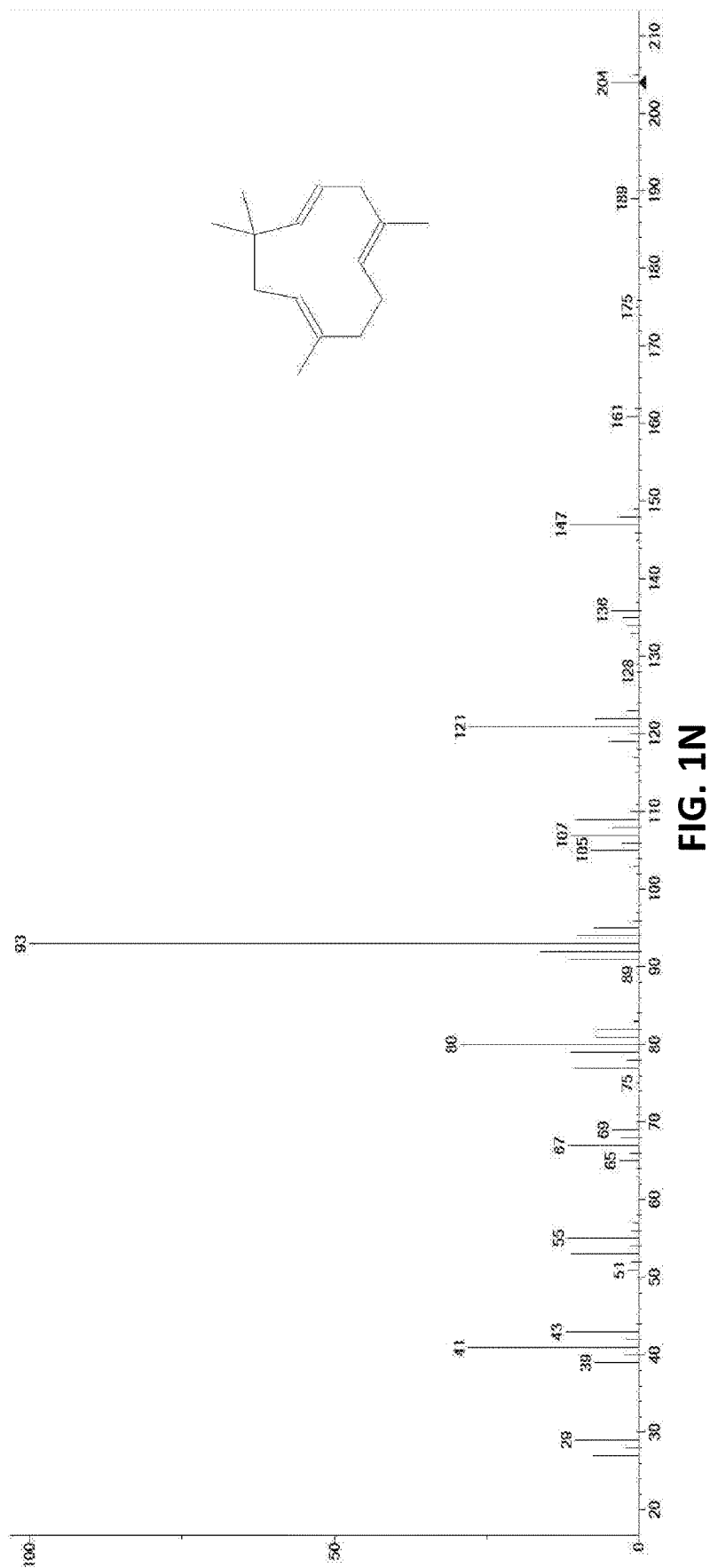
FIG. 1N. MS electron ionization fragmentation pattern for humulene, *Rhizopus arrhizus* var. *delemar*.
Figure 10:
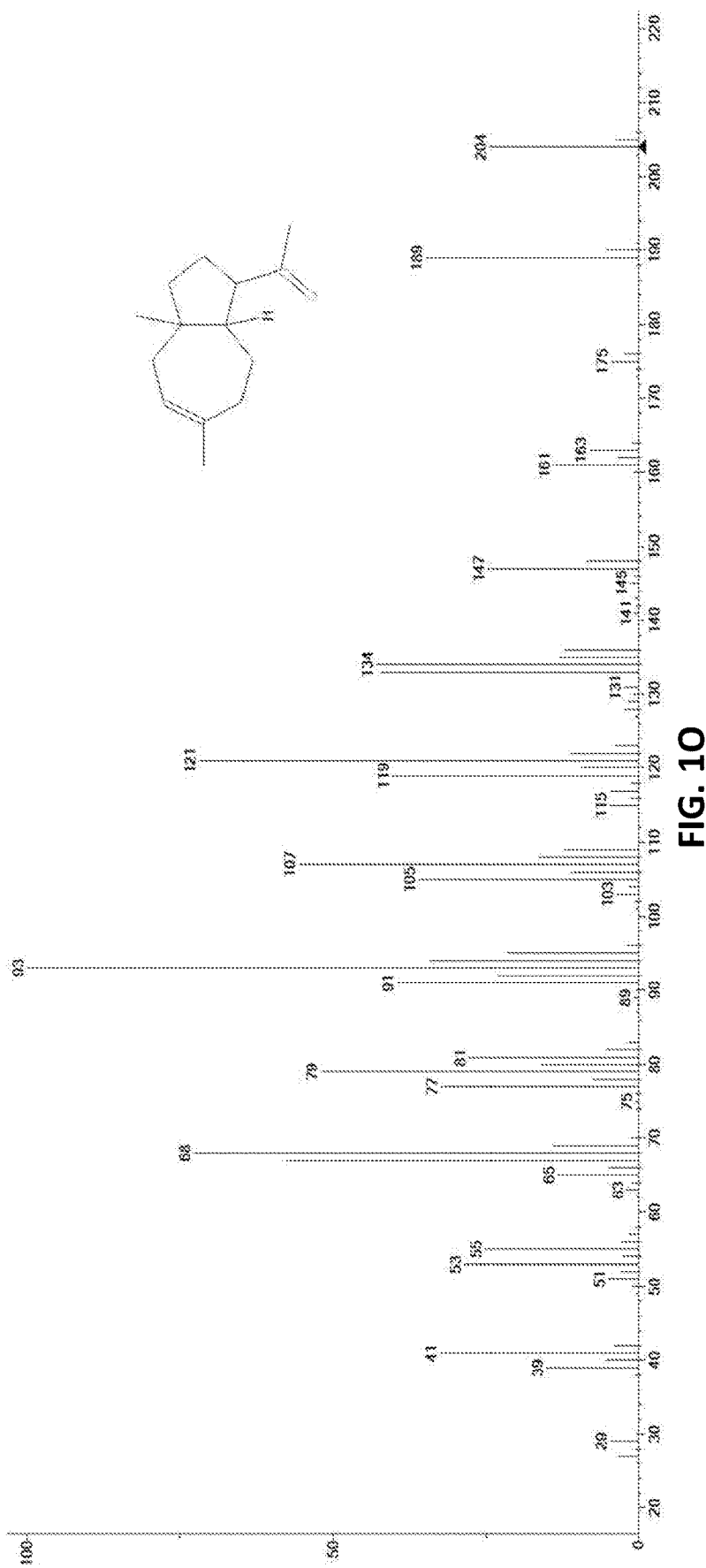
Figure 1P:
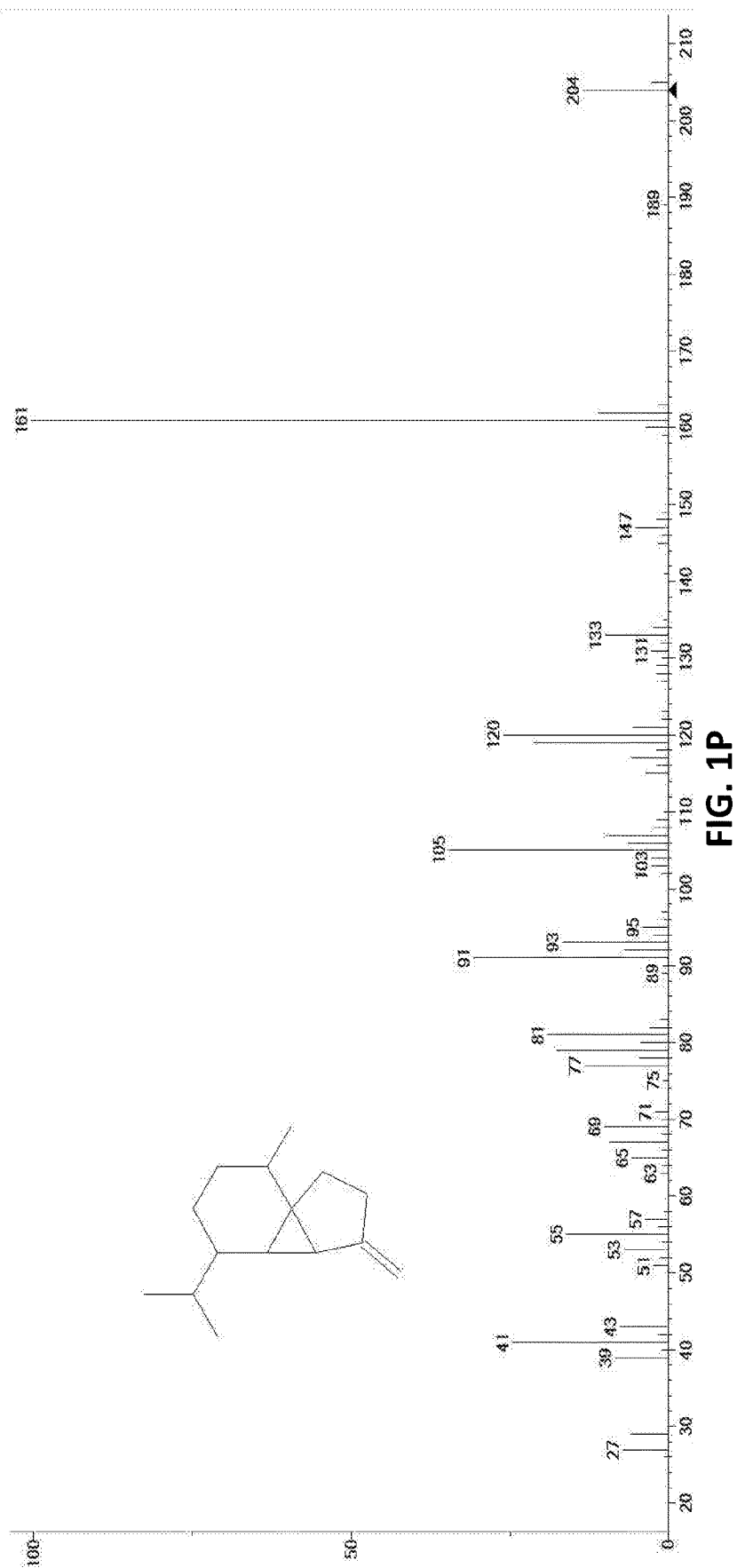
FIG. 1P. MS electron ionization fragmentation pattern for cubebene, *Rhizopus microsporus*.
Figure 1Q:
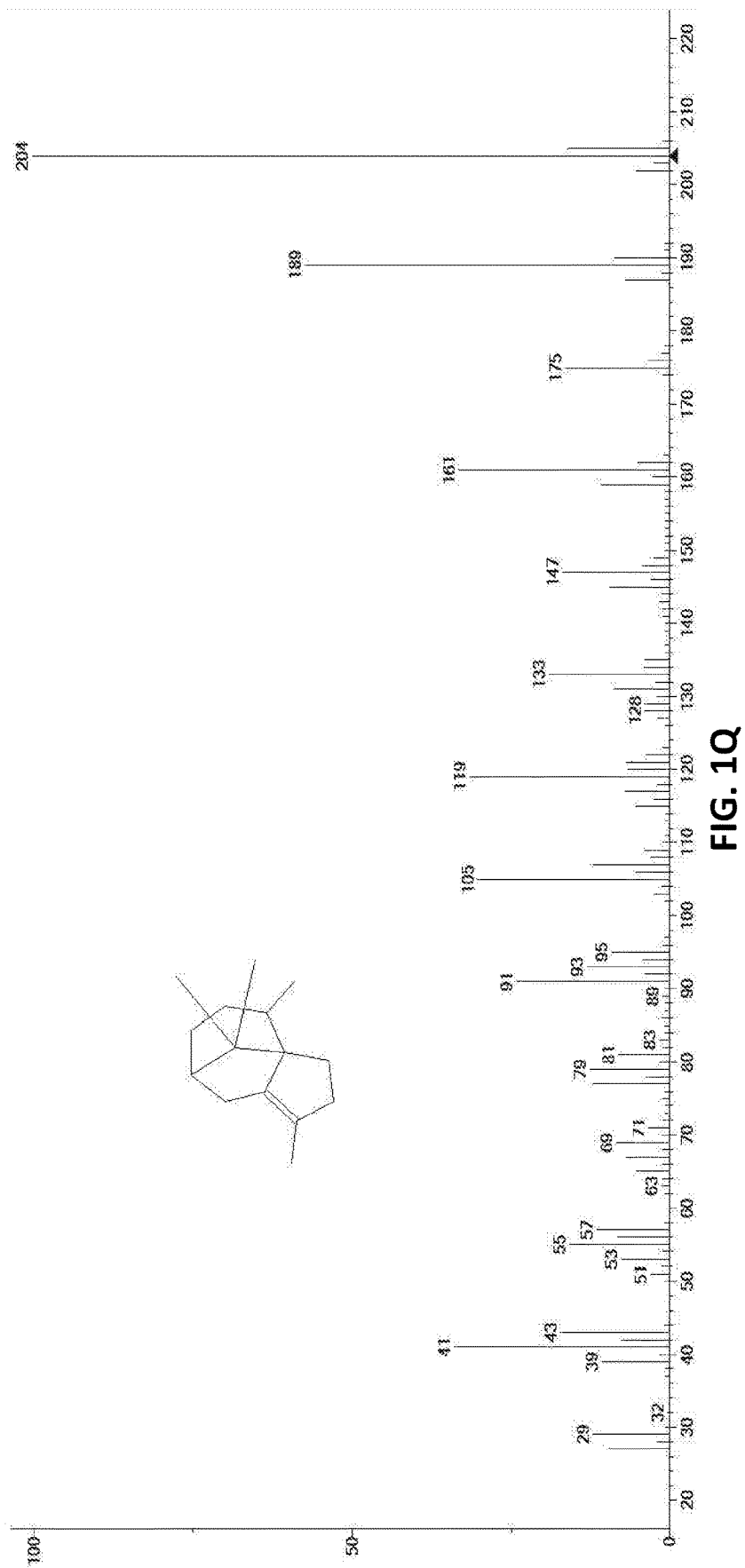
FIG. 1Q. MS electron ionization fragmentation pattern for cyperene, *Rhizopus microsporus*.
Figure 1R:
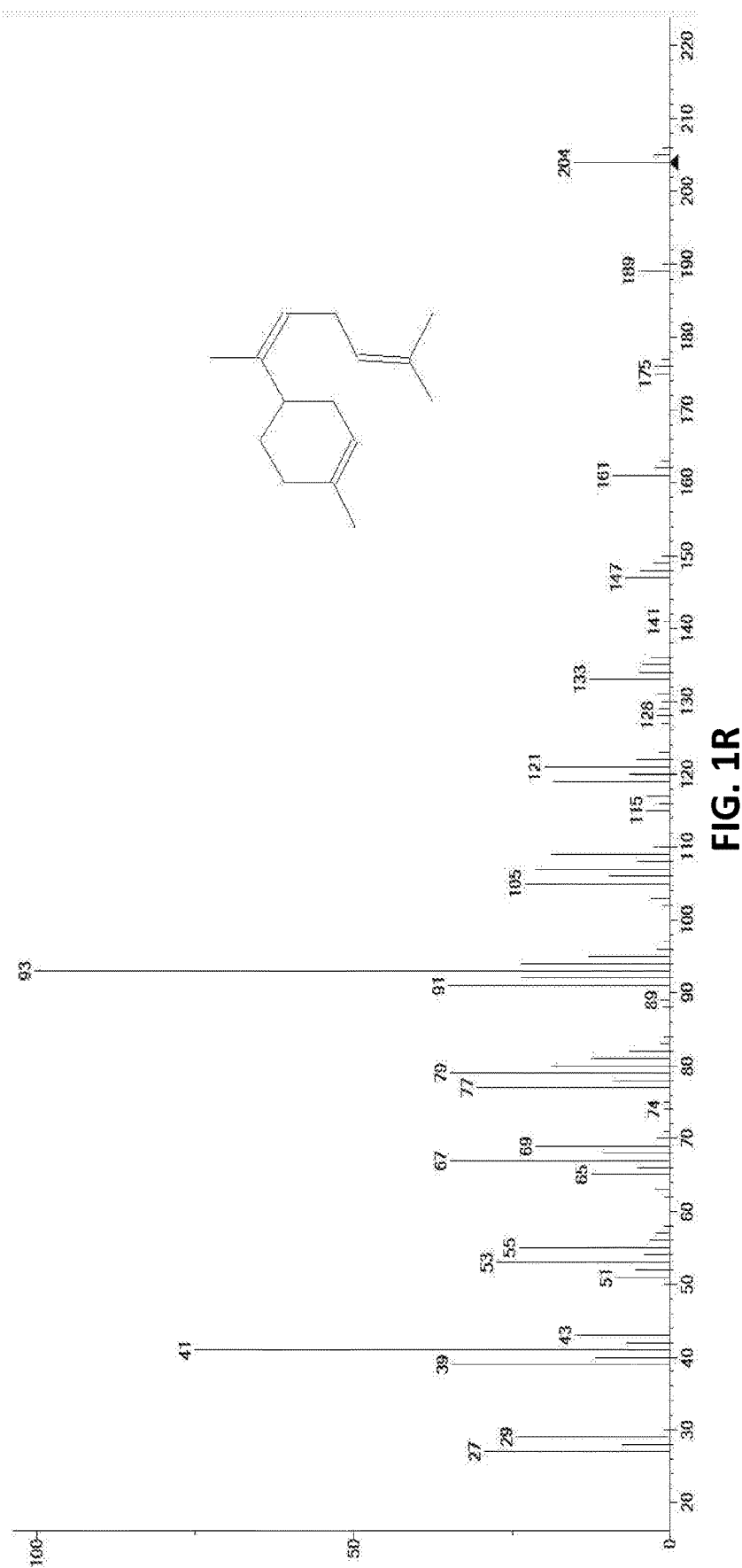
FIG. 1R. MS electron ionization fragmentation pattern for α-bisabolene, *Rhizopus microsporus*.

Pathogenic molds produce VOCs as part of their normal metabolism. As described herein, the present inventors have identified unique, species-specific VOC profiles of the most common pathogenic species of Mucorales fungi, including *Rhizopus arrhizhus* var. *arrhizus*, *Rhizopus arrhizhus* var. *delemar*, and *Rhizopus microsporus*, *Syncephalestrum racemosum*, and *Mucor circillenoides* that can be used to discriminate these species from each other and from other molds. A number of methods including differential mobility spectrometry (DMS) can be used for the rapid discrimination of fungal species using pattern-based identification of these species-specific VOC profiles.

Detection of these unique VOC profiles can be harnessed for species-level identification of Mucorales and other mold species in the laboratory, and direct detection of these fungal volatile profiles in the breath of patients with suspected mucormycosis can be used for the rapid, noninvasive, highly accurate, and species-specific diagnosis of mucoramycosis and other fungal pneumonias. The methods and devices described herein, e.g., the DMS-based detection methods, can be adapted to a small, portable bedside breath gas detection system for real-time patient breath surveillance for this pattern of fungal metabolites, to allow for earlier diagnosis than currently possible, more rational test-based prescribing of antifungal medications, monitoring of clinical response to antifungal therapy, and ultimately, better patient outcomes.

As described herein, among other uses, these VOC profiles can be used for:
a. rapid, noninvasive, sensitive, and species-specific breath tests for the diagnosis of mucormycosis and the discrimination of mucormycosis from aspergillosis and other causes of pneumonia in the growing population of immunocompromised patients at risk for invasive fungal infections;
b. surrogate marker demonstrating successful antifungal treatment of mucormycosis, and
c. rapid identification and antifungal susceptibility testing of Mucorales species, e.g., in the microbiology laboratory, based on their VOC profile (i.e., the VOCs present in the sample).

Mucormycosis

The methods described herein can be used to detect or diagnose mucormycosis in a subject, to select treatment and to treat mucormycosis, and to monitor treatment of mucormycosis. Mucormycosis refers to infection caused by diverse fungal species, including *Rhizopus*, *Rhizomucor*, and *Mucor*. Mucorales are environmentally ubiquitous fungi and can be commonly found in soil and in decaying matter; because of their low virulence they rarely cause disease except in individuals who are immunocompromised, e.g., due to a coexisting condition such as diabetes or cancer, or who are receiving medications that result in immunosuppression or neutropenia. The methods can be used in the different forms of mucormycosis, including infection of the facial sinus or nasal cavities and/or brain (e.g., rhinocerebral mucormycosis), as well as disseminated, pulmonary, cutaneous, and gastrointestinal mucormycosis (see, e.g., Walsh et al., Clinical Infectious Diseases 2008; 46:327-60; Milroy et al., J Clin Pathol. 1989 February; 42(2): 123-127). In preferred embodiments, the methods described herein can be used for subjects with rhinocerebral, sinus or nasal mucormycosis.

Samples

The methods described herein can be performed on a gas or liquid sample. In some embodiments, the sample is exhaled breath directly from an individual or from a breathing machine such as a ventilator. Alternatively, the methods can be performed using headspace from a culture known or suspected to include fungal, e.g., Mucorales species, e.g., commercially-available or lab-cultured species or species obtained from a primary sample from a subject, e.g., a clinical sample obtained by biopsy of the affected area (e.g., nasal biopsy, transthoracic percutaneous needle aspiration, or video assisted biopsy) or bronchoalveolar lavage. The sample is maintained in a suitable growth medium to allow growth and metabolism of any fungal, e.g., Mucorales, species in the sample. In certain embodiments, the invention involves taking a clinical sample from a subject and placing it in media, for example, with microfluidics, or in culture, for example, with conventional culturing methods. The fungal, e.g., Mucorales, species, if present, are stimulated to metabolize. The headspace (gaseous phase) generated as a result of this metabolism can be collected and analyzed using a method described herein or known in the art, see, e.g., US20100291617. In some embodiments, the methods are performed directly on nasal or bronchoalveolar washings, obtained by nasal/bronchoscopy/bronchoalveolar lavage. In some embodiments, the sample is a gas, e.g., patient breath or gas from the headspace of an in vitro culture sample. Where headspace gas is used, the gas should be collected after the headspace has been in contact with the culture for a sufficient amount of time for the compounds to be present, preferably in an air-tight, sealed environment.

The VOCs can also be detected in a liquid sample, since they are expected to be there in equilibrium with the gaseous phase. Thus, in addition to or as an alternative, the samples assayed using the methods described herein can include a liquid, e.g., blood (e.g., plasma or serum), lymph, urine, tears, saliva, sputum, nasal mucus, phlegm (e.g., expectorate), or CSF from a subject (e.g., from a biological fluid that comes near or preferably into contact with the tissue or organ that is known or suspected to be infected with a fungus, e.g. a Mucorales species), or the liquid phase (e.g., supernatant) of an in vitro culture. In some embodiments, the sample comprises saliva from the subject.

Detection Methods

A number of methods known in the art can be used to detect the presence of the VOCs described herein in a sample. Exemplary methods (particularly for use with a gas sample) include gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; electrochemical sensors; photoacoustic equipment; laser-based equipment; electronic noses (bio-derived, surface coated); and various ionization techniques. See, e.g., US20100291617 and US20070003996. Preferred methods include ion mobility spectrometry (IMS) or differential mobility spectrometry (DMS).

In some embodiments, the methods described herein include the use of differential mobility spectrometry to detect VOCs in a sample. An exemplary micro-machined differential mobility spectrometer (DMS), developed for chemical and biological sensing applications, is currently available from Sionex Corporation. DMS has several features that make it an excellent platform for VOC analysis: it is quantitative, selective, and exquisitely sensitive, with a volatile detection limit in the parts-per-trillion range (Davis et al., In: 12th International Conference on Transducers, Solid-State Sensors, Actuators and Microsystems; 2003; p. 1233-8 vol. 2; Miller et al., In: Solid-State Sensors and Actuators Workshop; 2000; Hilton Head, S.C.; 2000; Krebs et al., Sensors Journal, IEEE 2005; 5(4):696-703). Unlike mass spectrometry, which separates particles based on mass/charge ratios, DMS harnesses differences in ion mobility in low and high electric fields to achieve a gas-phase separation of ions at atmospheric pressure. DMS rapidly detects compounds that are difficult to resolve by other analytical techniques such as mass spectrometry in challenging matrices such as human breath (Kanu et al., J Mass Spectrom 2008; 43:1-22; Kanu et al., J Chromatogr A 2008; 1177:12-27; Luong J et al., J Chromatogr Sci 2006; 44:276-286; Nazarov et al., Anal Chem 2006; 7697-706; Kolakowski et al., Analyst 2007; 132:842-64).

DMS can be tuned to monitor specific ion masses, thus tailoring response characteristics to focus on various compounds of interest. It requires no reagents, generates the high fields required by the sensor using a small power supply, and has already been microfabricated, resulting in a small, portable machine that can be used at the bedside, with a turnaround time of several minutes. DMS has been used successfully in several commercial settings, including a hand-held, portable detector of trace levels of chemical warfare agents from General Dynamics (JUNO™) and airport explosives detectors from Thermo (see, e.g., U.S. Pat. No. 7,605,367). DMS technology has also been successfully applied to the characterization of unique VOCs produced by *Mycobacterium tuberculosis, Aspergillus* sp., and other pathogens (see, e.g., Fong et al., Anal Chem 2011; 83:1537-46; Shnayderman et al., Anal Chem 2005; 77:5930-7; WO 2014/039856; WO 2015/187938).

To perform a measurement using a DMS, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities. For other devices, measurements are performed using methods known in the art.

Additional non-limiting examples of systems that can be used in the present methods include those described in US20090078865; US20130168548; US20100291617 and US20070003996.

In some embodiments, the methods include obtaining a sample of ambient air and detecting the presence and/or levels of VOCs in the air, to provide a reference for subtraction of ambient VOCs.

A number of methods are known in the art for detecting the presence and/or levels of the VOCs in a liquid sample, including but not limited to chromatography (e.g., HPLC) and spectrophotometry (e.g., MS, LC-MS, MALDI-TOF, and other of the methods described above for gas-phase samples).

Combination Diagnostics

In some embodiments, the methods include performing an additional diagnostic test for a fungal infection, e.g., mucormycosis. A number of such tests are known in the art and include radiology imaging studies (e.g., CT imaging, e.g., of the paranasal sinuses and an endoscopic examination of nasal passages); bronchoalveolar lavage, transthoracic percutaneous needle aspiration; video assisted thoracoscopic biopsy; and biopsies of any suggestive lesions. PCR can be used for detection of DNA from common Mucorales species, e.g., as described in Millon et al., Clin Infect Dis. 2013; 56(10):e95-101 and Bernal-Martinez et al., Clin Microbiol Infect. 2013; 19(1):E1-7. A positive result on one of these tests can provide further evidence supporting a diagnosis of mucormycosis; see, e.g., Walsh et al., Clinical Infectious Diseases 2008; 46:327-60. A galactomannan enzyme immunoassay can also be performed to rule out invasive aspergillosis.

Mucorales Species Identification and Diagnosis

As described herein, *Rhizopus arrhizus* var. *arrhizus*, *Rhizopus arrhizus* var. *delemar*, and *Rhizopus microsporus* each produce VOCs that can be used to identify them in a sample, e.g., in a sample comprising breath of a subject, or headspace from a culture suspected of comprising a fungus; the culture can be, e.g., a culture of a biopsy from a subject, or a culture in a microbiology laboratory, e.g., a culture known or suspected of containing or being contaminated with a fungal species. This identification can be used to diagnose a subject with the specific species of the fungal infection, allowing for the administration of species-specific treatments, e.g., as described below.

Thus, the methods described herein can include obtaining a sample comprising breath of a subject, or headspace from a culture suspected of comprising a fungal species, e.g., Mucorales or *Aspergillus*, and detecting and identifying the VOCs in the sample. The methods can include detecting in headspace from a culture the presence of one, two, three, four or more of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene, which indicates the presence of a Mucorales fungi. For example, the presence of one, two, three or more of 1H-Indene, 2,3,3a,4-tetrahydro-3,3a, 6-trimethyl-1-(1-methylethyl)-, longipinene, cedrene, aromandendrene, alloaromadendrene, cubebol, and aciphyllene indicates the presence of *Rhizopus arrhizus* var. *arrhizus*. The presence of one, two, three or more of 1H-Indene, 2,3,3a,4-tetrahydro-3,3a,6-trimethyl-1-(1-methylethyl)-, isoledene, daucene, isocomene, isocaryophyllene, humulene, and isodaucene indicates the presence of *Rhizopus arrhizus* var. *delemar*. The presence of one, two, three or more of alloaromadendrene, cubebene, cyperene, and α-bisabolene indicates the presence of *Rhizopus* microsporus.

When the sample comprises breath from a patient suspected of being infected with Mucorales fungi, the methods can include detecting the presence of one, two, three, four or more of Cedrene; cedranoxide, 8, 14-; 1H-Indene,2,3,3a,4-tetrahydro-3,3a,6-trimethyl-1-(1-methylethyl)-; Longifolene; 2H-3,9a-Methano-1-benzoxepin; octahydro-2,2,5a, 9-tetramethyl-,[3R-(3α,5aα,9α,9aα)]-; cis-(–)2,4a,5,6,9a-Hexahydro-3,5,5,9-tetramethyl(1H)benzocycloheptene; selina-5,11-diene; or α-guaiene; alloaromadendrene indicates the presence of a Mucorales fungal infection.

In some embodiments, the presence of one, two, or all three of cedrene; cedranoxide, 8, 14-; and 1H-Indene, 2,3, 3a,4-tetrahydro-3,3a,6-trimethyl-1-(1-methylethyl)- in the breath of a patient indicates the presence of a Mucorales fungal infection, e.g., *Rhizopus*.

In some embodiments, the presence of one, two, three, or all four of 1H-Indene, 2,3,3a,4-tetrahydro-3,3a,6-trimethyl-1-(1-methylethyl)-; cedrene; selina-5,11-diene; and cedranoxide, 8,14- in the breath of a patient indicates the presence of a Mucorales fungal infection, e.g., *Rhizopus*.

In some embodiments, the presence of one, two, three, or more of longifolene; 2H-3,9a-Methano-1-benzoxepin; octahydro-2,2,5a,9-tetramethyl-,[3R-(3α,5aα,9α,9aα)]-; and cis (–)2,4a,5,6,9a-Hexahydro-3,5,5,9-tetramethyl(1H)benzocycloheptene indicates the presence of *Rhizopus arrhizus* var. *arrhizus*; one, two, or all three of cedrene; selina-5,11-diene; and cedranoxide, 8, 14-indicates the presence of *Rhizopus microsporus*; and the presence of α-guaiene and alloaromadendrene indicates the presence of *Rhizopus arrhizus* var. *delemar*.

In some embodiments, the presence of one, two, or all three of cedrene; cedranoxide, 8, 14-; and 1H-Indene, 2,3, 3a,4-tetrahydro-3,3a,6-trimethyl-1-(1-methylethyl)- in the breath of a patient indicates the presence of a Mucorales fungal infection, e.g., *Rhizopus*.

In some embodiments, the presence of one, two, three, or all four of 1H-Indene, 2,3,3a,4-tetrahydro-3,3a,6-trimethyl-1-(1-methylethyl)-; cedrene; selina-5,11-diene, and cedranoxide, 8,14- in the breath of a patient indicates the presence of a Mucorales fungal infection, e.g., *Rhizopus*.

Differential Diagnosis: Aspergillosis

Where differential diagnosis between mucormycosis and aspergillosis is desired, the methods can include those described in WO 2014/039856 and WO 2015/187938, e.g., detecting and identifying the VOCs in the sample, and detecting the presence a VOC associated with a Mucorales fungus as described herein, and/or the presence of one, two, three, or more, e.g., all, of camphene, alpha-pinene, beta-pinene, limonene, alpha-bergamotene, beta-trans-bergamotene, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, alpha-bergamotene, or beta-trans-bergamotene indicates the presence of *A. fumigatus* in the sample (and thus an *A. fumigatus* infection in cases where the sample is from a subject); the presence of one, two, three, or more, e.g., all, of elixene, alpha-santalene, beta-elemene, acoradien, chamigrene, and 1,5,9-trimethyl cyclododecatriene indicates the presence of *A. terreus* in the sample (and thus an *A. terreus* infection in cases where the sample is from a subject); and the presence of one or both of 9-decene-2-one and beta-sesquiphellandrene indicates the presence of *A. calidoustus* in the sample (and thus an *A. calidoustus* infection in cases where the sample is from a subject). In some embodiments, where limonene or alpha-pinene is present, at least one or two other VOCs must also be present for a positive species identification, and a species-specific diagnosis, to be made.

Methods of Treatment

The methods described herein can be used to select a treatment for a subject, and can optionally include administering the treatment to a subject and monitoring the efficacy thereof. When a subject has been diagnosed by a method described herein as having mucormycosis or IA, then a treatment comprising administration of a therapeutically effective amount of an antifungal compound can be administered.

A number of antifungal compounds are known in the art and under development. At present, deoxycholate amphotericin B (D-AMB) and its lipid formulations (AMB lipid complex (ABLC), liposomal amphotericin B (LAMB), and Amphotericin B cholesteryl sulfate complex (AMB colloidal dispersion, ABCD)); azole compounds (itraconazole, voriconazole, posaconazole, isavuconazole); and echinocandins (caspofungin, micafungin, anidulafungin) are in clinical use, though voriconazole, isavuconazole, and D-AMB are the only compounds approved for primary treatment of invasive aspergillosis in the United States. For detailed information on treatment of mucormycosis and IA, see, e.g., Walsh et al., Clinical Infectious Diseases 2008; 46:327-60; Spellberg et al., "Recent advances in the management of mucormycosis: from bench to bedside." Clin Infect Dis. 2009 Jun. 15. 48(12):1743-51; Spellberg and Ibrahim, "Recent advances in the treatment of mucormycosis." Curr Infect Dis Rep. 2010 Nov. 12(6):423-9 and Marr et al., *Treatment and prevention of invasive aspergillosis*, Up-To-Date (topic updated on Oct. 18, 2012; literature review August 2013; available at uptodate.com/contents/treatment-and-prevention-of-invasive-aspergillosis?topicKey=ID%2F2459&elapsedTimeMs=7&view=print&displayedView=full). See also Crum-Cianflone et al., "Mucormycosis," Apr. 3, 2015, emedicine.medscape.com/article/222551.

In some embodiments, the methods include selecting and optionally administering an azole antifungal, e.g., itraconazole (ITR), voriconazole (VOR), posaconazole (POS), or isavuconazole (ISA), or an amphotericin B (AMB) formulation as described above, to a subject identified by a method described herein as having mucormycosis or IA. In some embodiments, the methods include administering an echinocandin, e.g., caspofungin, micafungin or anidulafungin, e.g., alone or in combination with an azole (e.g., voriconazole) or AMB.

It is known that triazoles are not active against some isolates of *A. calidoustus*, and some *A. terreus* isolates are resistant to AMB. See, e.g., Baddley et al., J. Clin. Microbiol. 2009, 47(10):3271. Thus, in some embodiments, where the species of *Aspergillus* is determined, an azole compound (e.g., ITR, VOR, POS, or ISA) is selected for (and optionally administered to) a subject who has *A. fumigatus* or *A. terreus*, but not *A. calidoustus*. In some embodiments, an AMB (e.g., D-AMB, ABLC, LAMB, or ABCD) is selected for (and optionally administered to) a subject who has *A. calidoustus*. In some embodiments, an AMB is selected for (and optionally administered to) a subject who has *A. fumigatus*, but not a subject who has *A. terreus*.

In some embodiments, the methods described herein can be used to determine susceptibility of *Aspergillus* species, e.g., to treatment with a known or suspected antifungal, e.g., in the microbiology laboratory. A sample suspected or known to include *Aspergillus* from a subject is obtained and cultured as described above, e.g., under conditions mimicking the in vivo environment, and then exposed to a potential treatment (e.g., a known or experimental treatment). After exposure to the treatment, the VOCs present in the headspace of the culture are sampled. If the treatment decreases VOCs as compared to a reference level (e.g., a level of VOCs in the headspace before exposure to the treatment), then the *Aspergillus* in the sample is considered susceptible to the treatment. In this case, the treatment is likely to be effective in treating mucormycosis in the subject; the treatment can be selected and optionally administered to subject.

Monitoring Treatment Efficacy

As described herein, successful treatment of a mucormycosis infection results in a decrease in fungal VOCs. Thus, the methods can include repeated assays of VOC levels in a subject, e.g., before, during, and after administration of a treatment for mucormycosis. A decrease in VOC levels would indicate that the treatment has been successful. In some embodiments, levels of one, two, or all three of cedrene; cedranoxide, 8, 14-; and 1H-Indene, 2,3,3a,4-tetrahydro-3,3a,6-trimethyl-1-(1-methylethyl)- are determined. A reduction in levels over time indicates that the treatment is effective. No reduction, or an increase in levels over time, indicates that the treatment is ineffective, and thus an increased dose or a different treatment can be administered.

Methods of Identifying Novel Antifungal Agents

Included herein are methods for screening test compounds, e.g., polypeptides, polynucleotides, inorganic or organic large or small molecule test compounds, to identify agents useful in the treatment of mucormycosis.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising one or more Mucorales species, and the ability of the test compound to decrease levels of a VOC as described herein in the headspace of the culture is determined.

In some embodiments, the test sample is, or is derived from (e.g., a sample taken from) an in vivo model of a disorder as described herein. For example, an animal model, e.g., a rodent (such as a rat or mouse) that has been infected with one or more Mucorales species can be used.

A test compound that has been screened by a method described herein and determined to decrease VOCs, can be considered a candidate compound. A candidate compound that has been screened, e.g., in an in vivo model of a disorder, e.g., a rodent infected with one or more Mucorales species, and determined to decrease VOCs in a sample comprising breath from the infected animal model or headspace from a culture of a sample from the infected animal model, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that decrease fungal VOCs in an animal model) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating mucormycosis. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of mucormycosis, as described herein. The animal can be monitored for a change in the disorder, e.g., for an improvement in a parameter of the disorder, e.g., a parameter related to clinical outcome. In some embodiments, the parameter is VOCs or survival, and an improvement would be a reduction in VOCs or an increase in survival. In some embodiments, the subject is a human, e.g., a human with mucormycosis and the parameter is levels of fungal VOCs or survival.

EXAMPLES

The invention is further described in the following examples, which do not limit the scope of the invention described in the claims.

Materials and Methods

The following materials and methods were used in the Examples below.

In Vitro Testing of Mucorales species: We characterized the in vitro volatile metabolite profile of clinical strains of fungi from the order Mucorales, all of which had molecular confirmation of their species identity by ITS and D1/D2 sequencing. We selected three species that most commonly cause human invasive mucormycosis, including *Rhizopus arrhizus* var. *arrhizus* (N=8), *Rhizopus arrhizus* var. *delemar* (N=7), and *Rhizopus microsporus* (N=3).

Fungal Culture and Headspace Extraction Conditions: We inoculated $10^6$ conidia from each species into 5 mL of YPD broth (Teknova, Hollister, Calif.) in a 20-mL glass vial sealed with an airtight cap incorporating a silicone septum (Restek Corporation, Bellefonte, Pa.), with concurrent media controls, in sets of 4 technical replicates each for each fungal species. We incubated each vial at 37° C. for 72-96 hours in an orbital shaker at 250 rpm to promote hyphal growth and prevent conidiation. After heating each vial to 80° C. for 30 minutes to increase the concentration of sesquiterpene metabolites in the gas phase of the vial, we adsorbed headspace gas over 4 minutes per sample onto thermal desorption tubes containing tandem beds of Tenax TA (200 mg), Carbograph 1 TD (100 mg), and Carboxen 1003 (100 mg) (Markes International, Llantrisant, United Kingdom), to retain polar and nonpolar VOCs over a wide range of boiling points.

In Vivo Testing of Mucorales species: We examined the in vivo volatile metabolite profile of *Rhizopus arrhizus* var. *arrhizus*, *Rhizopus arrhizus* var. *delemar*, and *Rhizopus microsporus* in a mouse model. We induced neutropenia in 25-28 g female balb/c mice by intraperitoneal cyclophosphamide injections (200 mg/kg 4 days prior to infection and 150 mg/kg 1 day prior to infection) and suppressed pulmonary macrophage function with 300 mg/kg cortisone acetatex1 one day prior to infection. Mice were infected intranasally with $10^6$ conidia from each of these Mucorales species. Three days later, we performed a tracheostomy on each mouse and ventilated these animals with 10-12 mg/kg of air through a murine ventilator, collecting breath samples from each mouse and examining these breath samples using thermal desorption-gas chromatography/mass spectrometry and gas chromatography-differential mobility spectrometry. We also collected breath samples from patients with suspected invasive mucormycosis over 4 minutes per sample onto thermal desorption tubes containing tandem beds of Tenax TA (200 mg), Carbograph 1 TD (100 mg), and Carboxen 1003 (100 mg) (Markes International, Llantrisant, United Kingdom).

GC-MS/MS methods: We thermally desorbed volatile metabolites onto an automated thermal desorption unit (TD-100, Markes International) at 290° C. for 5 minutes with helium carrier gas at a flow rate of 40 mL/min. Volatile analytes were concentrated onto a TD-100 air toxics cold trap (U-T15ATA-2S, Markes International), which was rapidly heated to 300° C. to deliver volatile metabolites, with a 10:1 split ratio, to a Vf-624 ms capillary column (30 m×0.25 mm, 6% cyanopropyl/phenyl, 94% polydimethylsiloxane, film thickness 1.4 µm, Agilent Technologies, Santa Clara, Calif.) with a gas chromatograph (GC) inlet temperature of 250° C. and a GC temperature program of 40° C. for 3 minutes raised to 70° C. at a rate of 5° C. per minute and held for 3 minutes, raised to 203° C. at 7° C. per minute and held for 4 minutes, then rapidly raised to 270° C. and held for 5 minutes. A triple quadrupole mass spectrometry (MS) detector (Agilent 7000A, Agilent Technologies, Santa Clara, Calif.) was used to analyze and identify VOCs, with a MS source temperature of 230° C., MS quad temperature of 150° C., and an electron ionization parameter of 1412 eV. A mass range m/z 40-550 was measured with a threshold of 150. We used identical conditions for our GC-MS/MS analysis after recollecting each sample onto the same sorbent tube, filtering for precursor ion 204>161, 133, 119, 107, and 93 with a voltage of 5 and 15 eV, 204>, with a voltage of 5 and 15 eV, 202>159 and 145 with a voltage of 5 and 15 eV, and 194>136 and 105 with a voltage of 5 and 15 eV.

Confirmation of metabolite identity: We used the National Institute of Standards and Technology (NIST) 14 Mass Spectral Library (Scientific Instrument Services, Ringoes, N.J.) for provisional identification of sesquiterpene/sesquiterpene derivative GC-MS peaks in the total ion chromatogram of each culture and media control, with comparison to Kovats retention indices.

GC-DMS methods: We extracted the headspace volatile organic compounds of heated Mucorales cultures from 180-240 seconds onto a GC-DMS Microanalyzer instrument equipped with a multibed sorbent tube and 30 meter, 0.25 mm internal diameter Vf624 GC column, at a pump rate of 100 mL/minute, repressurizing each headspace vial with an equal flow (100 mL/min) of high-purity nitrogen gas for the duration of each headspace extraction. Using a sorbent trap temperature program of 40° C. at baseline, ramping quickly from 0-5 seconds to 300° C. and staying at 300° C. for 60 seconds to allow release of volatile organic analytes retained on the sorbent tube onto the GC column, followed by a GC thermal program of 60° C. at baseline, ramping from 60° C. to 160° C. over 90 seconds, and remaining at 160° C. from 90-1300 seconds, with detection of analyte ions on the DMS detector. We used a scanning method with a starting compensation voltage of −30 and an ending compensation voltage of 10 with 101 steps of 0.4V each (each step duration was 10 milliseconds with a step settle time of 3 ms and each scan duration 1.01 seconds), a sensor temperature of 25° C., and a Rf voltage of 1200V, with recording of positive and negative DMS spectra by the detector. We also analyzed breath samples, collecting 240 seconds of regular tidal breathing directly onto this GC-DMS Microanalyzer instrument, using a GC thermal program of 60° C. at baseline, ramping from 60° C. to 150° C. over 90 seconds, and remaining at 150° C. from 90-1800 seconds.

Example 1. Definition of Mucorales VOC Profiles In Vitro

Figure 2A:
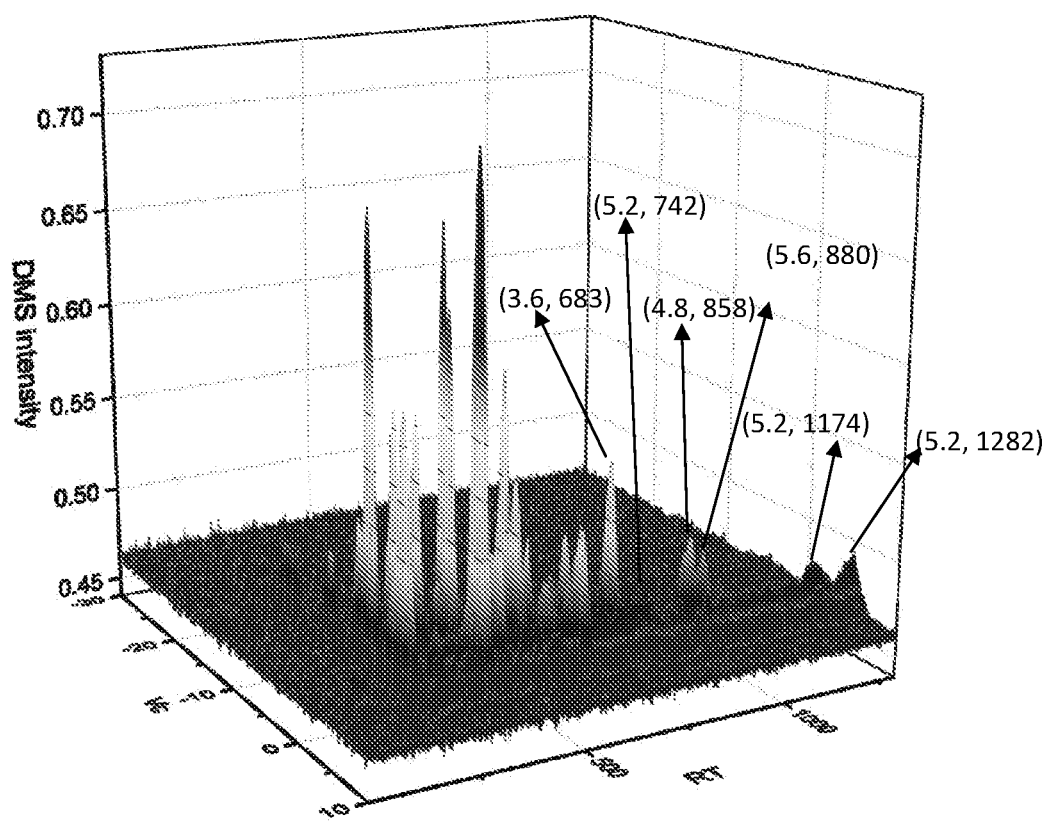
FIG. 2A. GC-DMS profile of *Rhizopus arrhizus* var. *arrhizus* in vitro. Axes are compensation voltage (Vc) vs. retention time (RT, in milliseconds) vs. DMS signal intensity. Coordinates represent (compensation voltage, retention time).
Figure 2B:
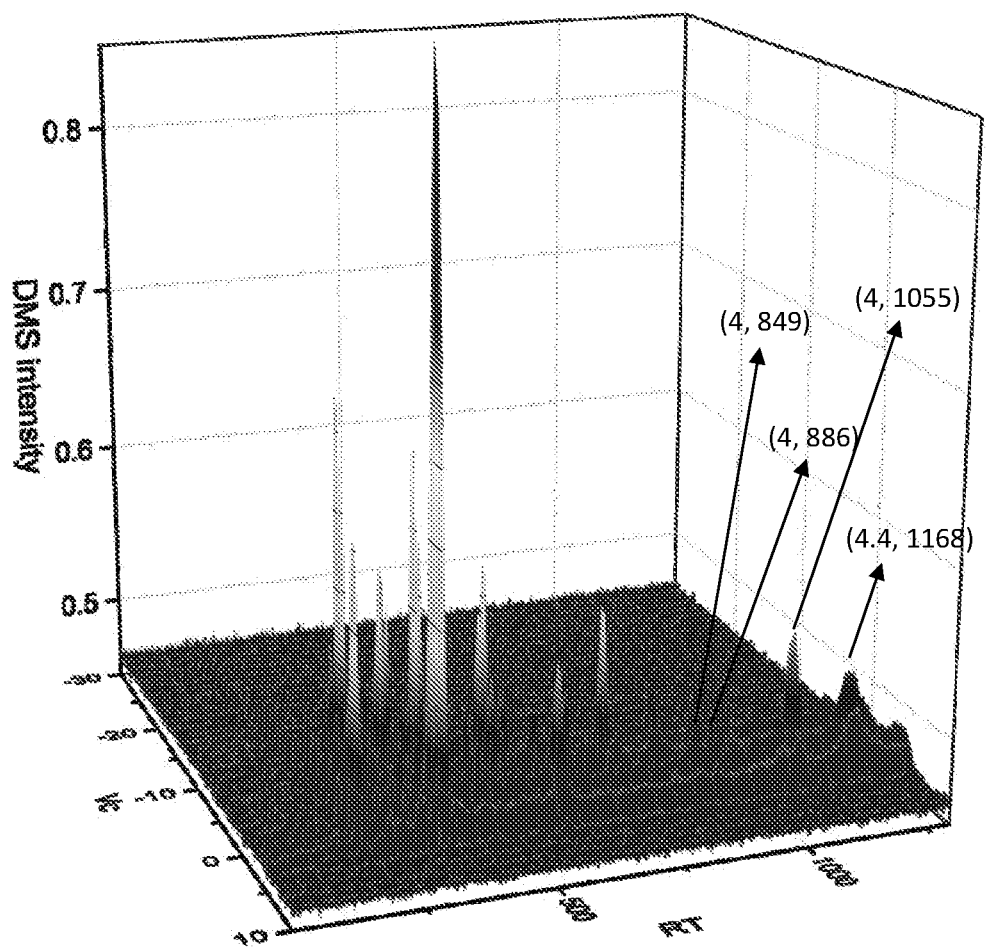
FIG. 2B. GC-DMS profile of *Rhizopus arrhizus* var. *delemar*, in vitro. Axes represent compensation voltage (Vc) vs. retention time (RT, in milliseconds) vs. DMS signal intensity. Coordinates represent (compensation voltage, retention time).
Figure 2C:
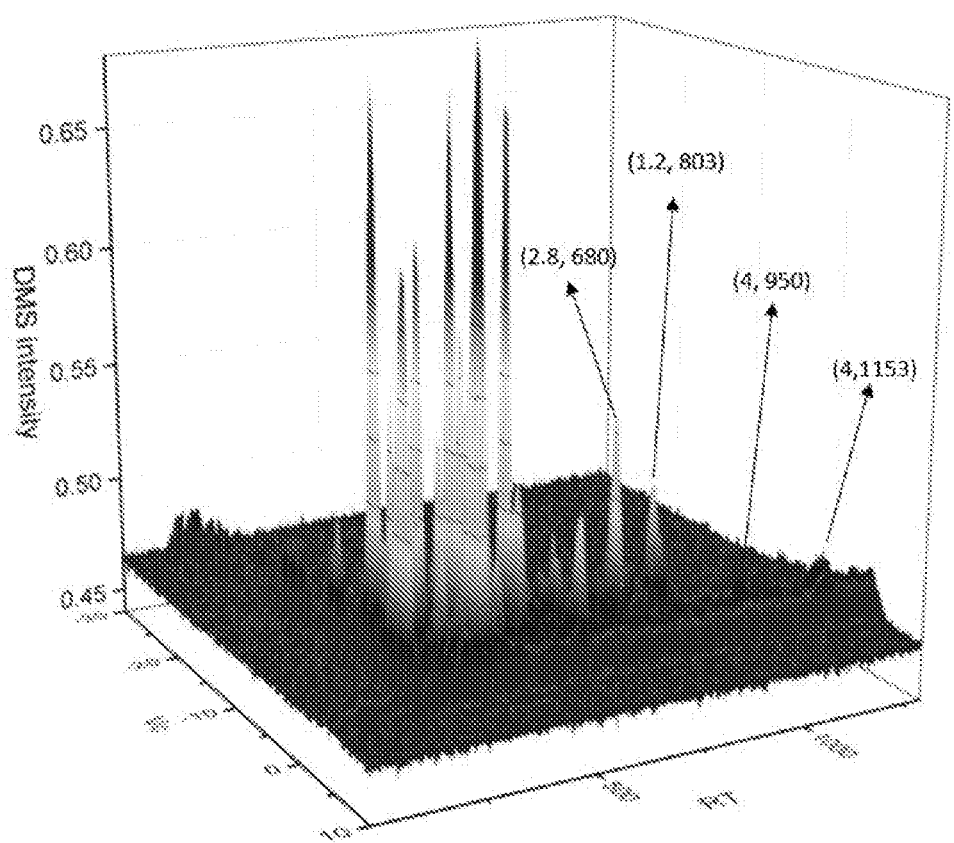
FIG. 2C. GC-DMS profile of *Rhizopus microsporus*, in vitro. Axes represent compensation voltage (Vc) vs. retention time (RT, in milliseconds) vs. DMS signal intensity. Coordinates represent (compensation voltage, retention time FIGS. 3A-I. In vivo breath secondary metabolite signature of infection in a murine model with *Rhizopus arrhizus* var. *arrhizus*, *Rhizopus arrhizus* var. *delemar*, and *Rhizopus microsporus*. Peaks are: (1) Cedrene, (2) Selina-5,11-diene (3) Cedranoxide, 8,14-, (4) β-Isocomene, (5) Epicubebol, (6) γ-Patchoulene, with MS fragmentation patterns presented in FIGS. 3B-3I, as follows: 3B, Cedrene; 3C, Selina-5,11-diene; 3D, Cedranoxide, 8,14-; 3E, Longifolene; 3F, 2H-3,9a-Methano-1-benzoxepin, octahydro-2,2,5a,9-tetramethyl-, [3R-(3α,5aα,9α,9aα)]-; 3G, cis-(-)2,4a,5,6,9a-Hexahydro-3,5,5,9-tetramethyl(1H) benzocycloheptene; 3H, α-Guaiene; and 3I, Alloaromadendrene.
Figure 3A:
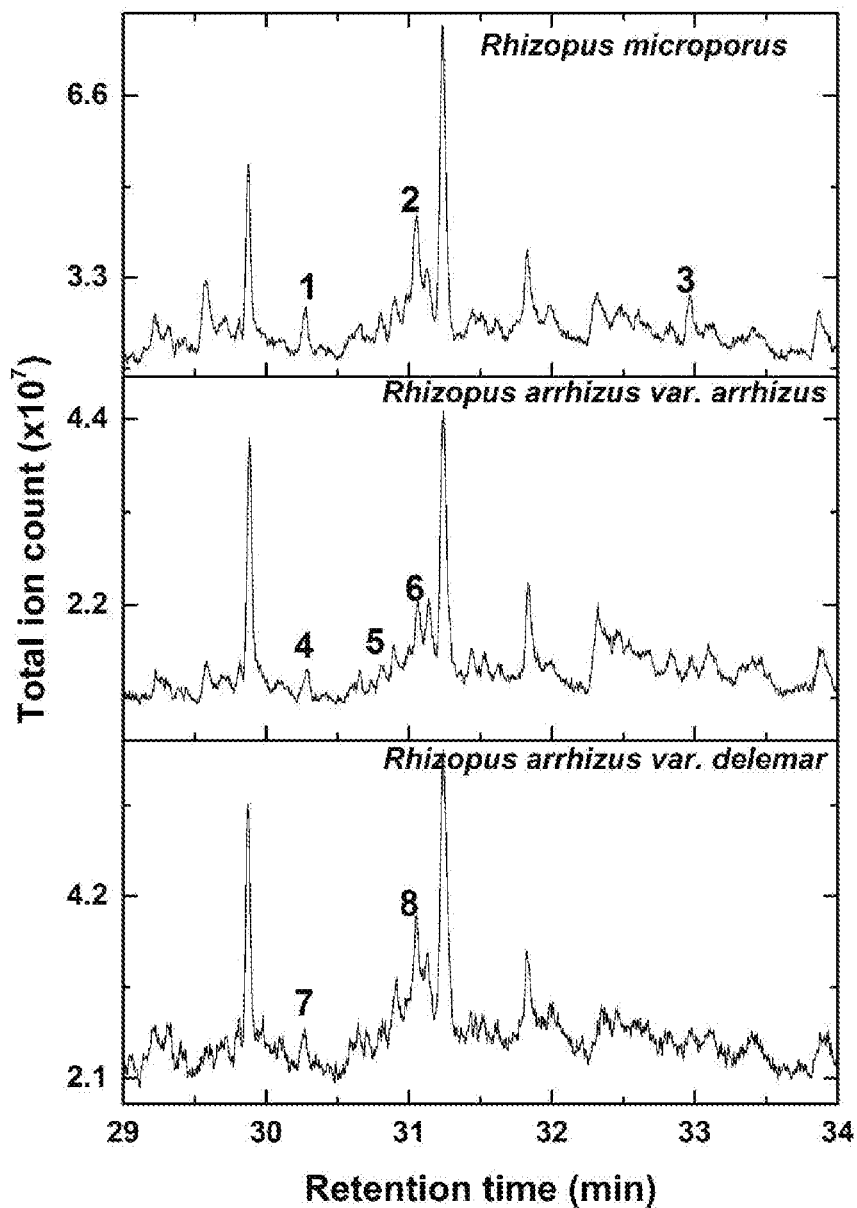
Figure 3B:
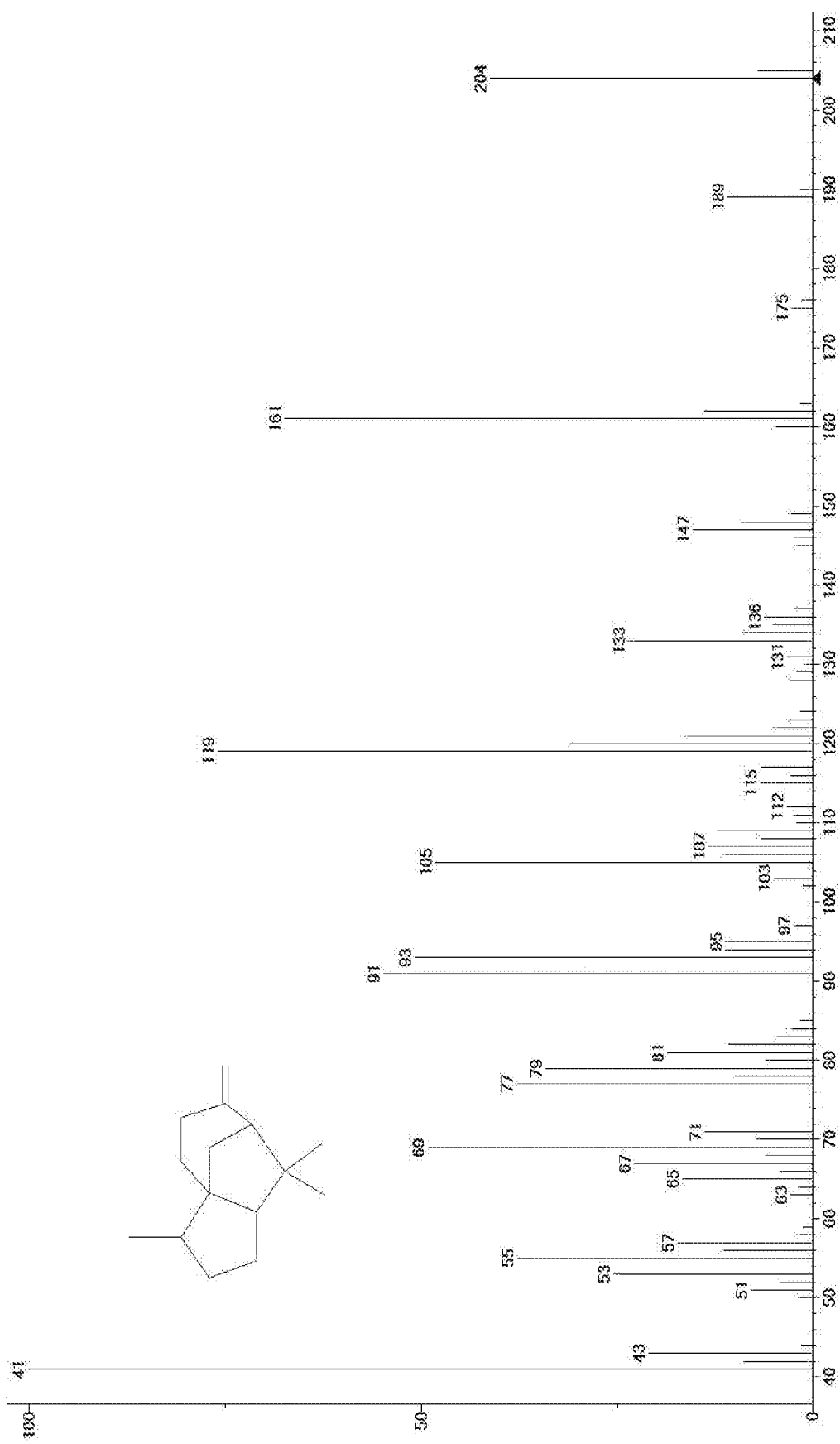
Figure 3C:
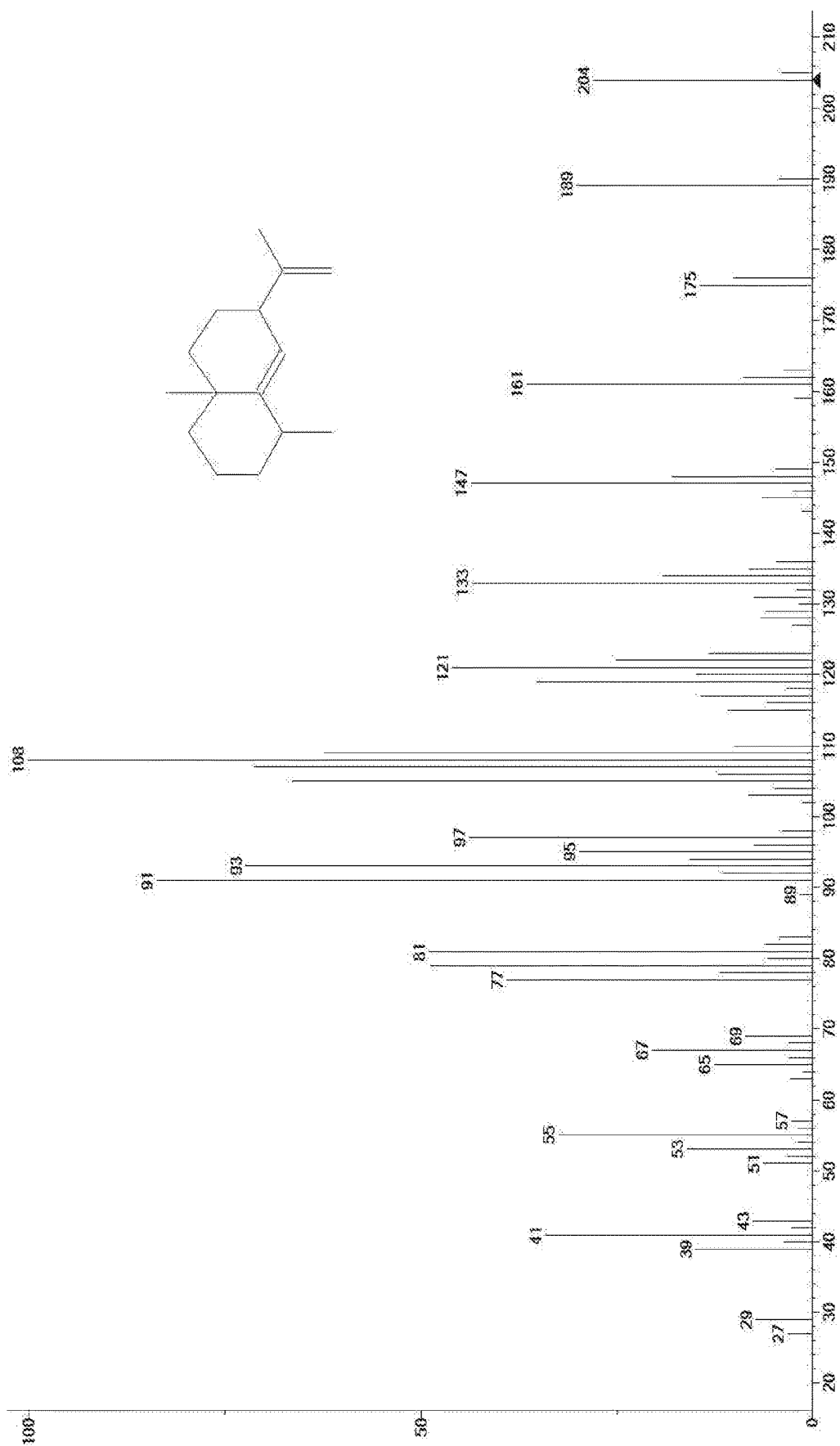
Figure 3D:
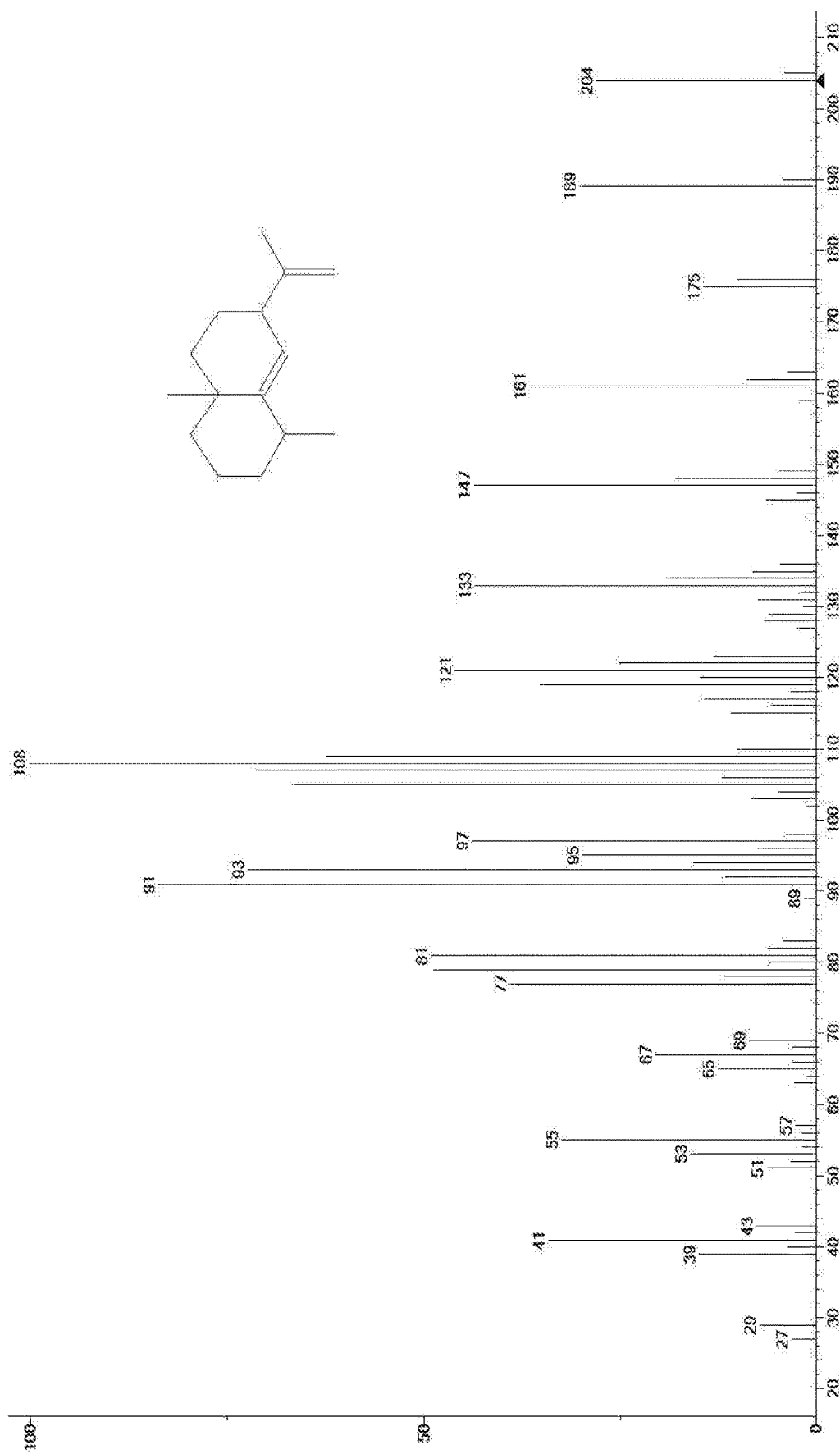
Figure 3E:
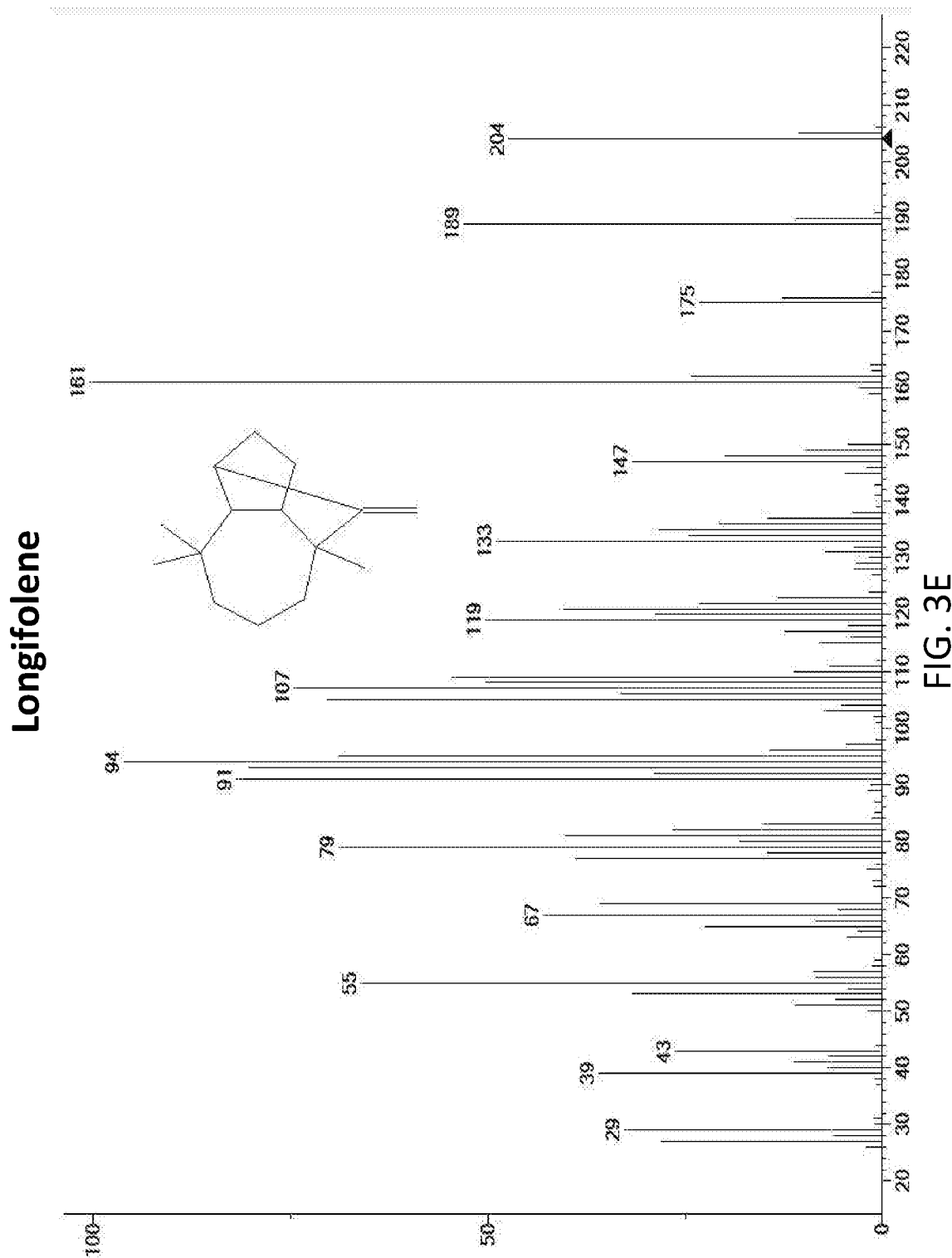
Figure 3F:
Figure 3H:
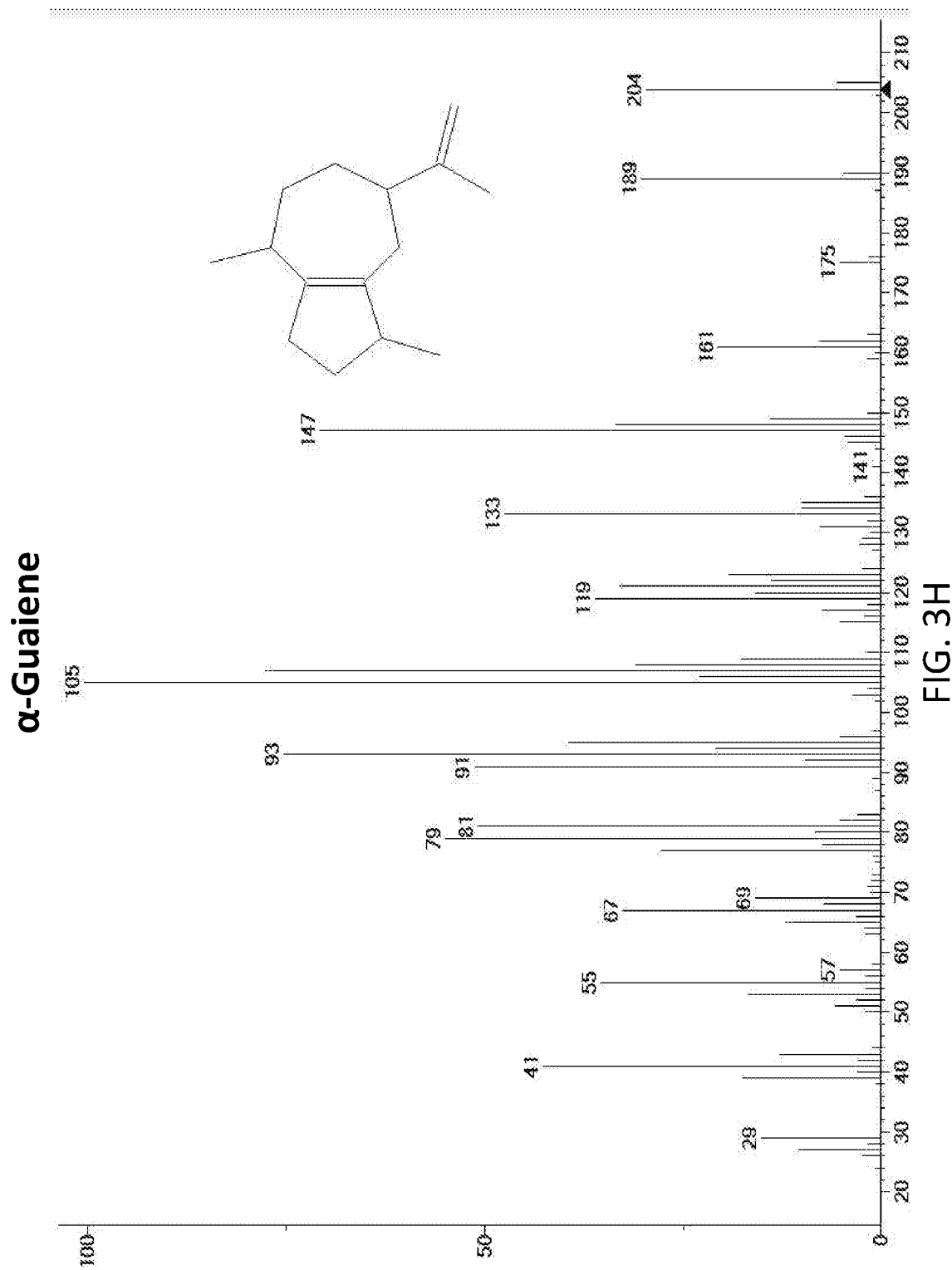
Figure 31:
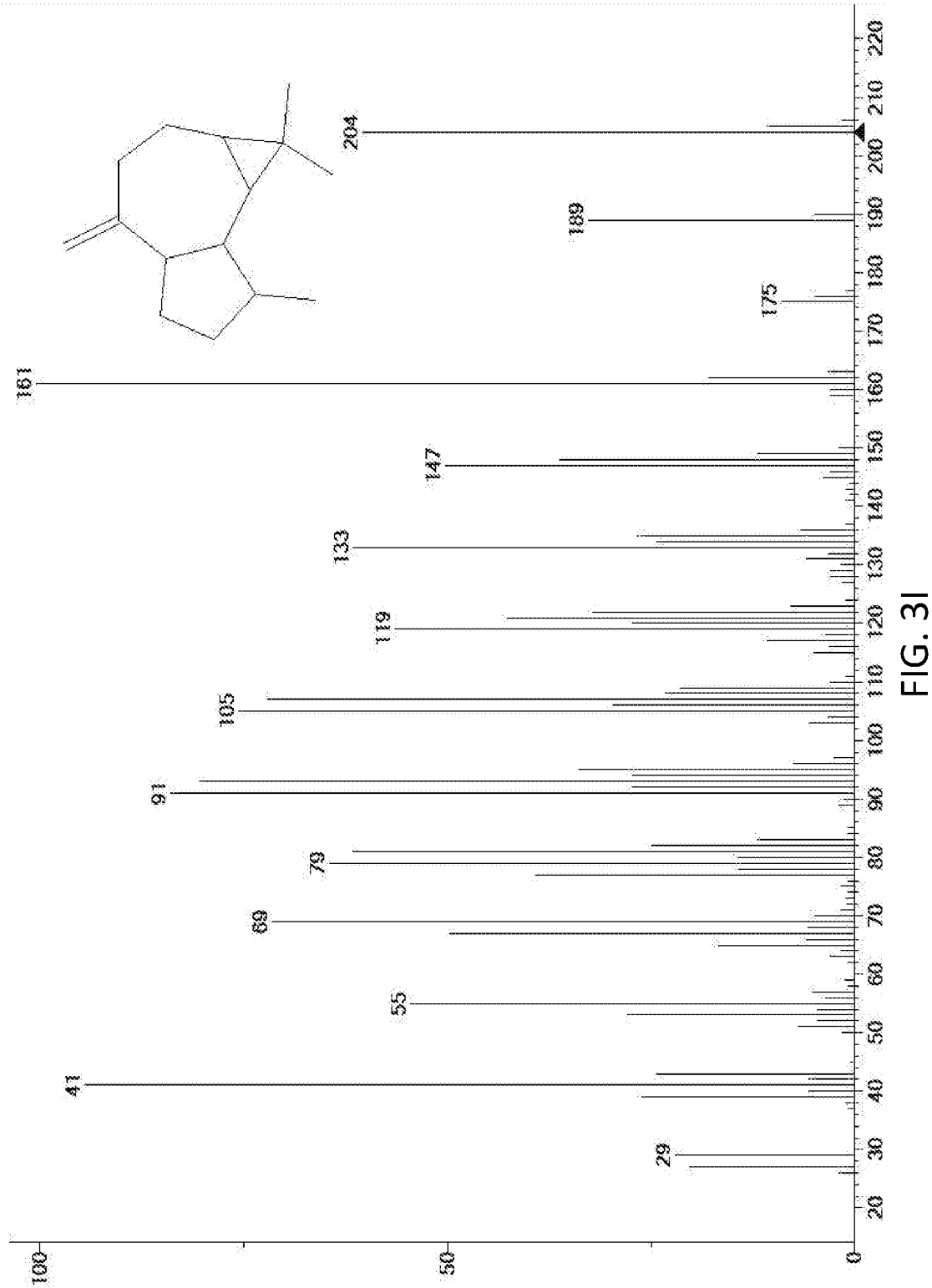

We identified a profile of 1H-Indene, 2,3,3a,4-tetrahydro-3,3a,6-trimethyl-1-(1-methylethyl)-, longipinene, cedrene, aromandendrene, alloaromadendrene, cubebol, and aciphyllene in *Rhizopus arrhizus* var. *arrhizus* (FIGS. 1A-I), with a corresponding GC-DMS signature as presented in FIG. 2A. For *Rhizopus arrhizus* var. *delemar*, we identified a profile of 1H-Indene, 2,3,3a,4-tetrahydro-3,3a,6-trimethyl-1-(1-methylethyl)-, isoledene, daucene, isocomene, isocaryophyllene, humulene, and isodaucene (FIGS. 1A, 1B, and 1J-1O), with a corresponding GC-DMS signature in FIG. 2B. In *Rhizopus microsporus*, we identified a profile of alloaromadendrene, cubebene, cyperene, and α-bisabolene (FIGS. 1A, 1F, and 1P-1R), with a corresponding GC-DMS signature in FIG. 2C.

Example 2. Definition of Mucorales VOC Profiles in In Vivo Breath Samples

Fungi shifted their metabolism substantially in vivo, with the overlay of the host environment and host immune responses. We identified a consistent secondary metabolite signature of longifolene, 2H-3,9a-Methano-1-benzoxepin, octahydro-2,2,5a,9-tetramethyl-, [3R-(3α,5aα,9α,9aα)]-, and cis(−)2,4a,5,6,9a-Hexahydro-3,5,5,9-tetramethyl(1H) benzocycloheptene in the breath of mice infected with strains of *Rhizopus arrhizus* var. *arrhizus*; a consistent breath signature of cedrene, selina-5,11-diene, and cedranoxide, 8, 14- in the breath of mice infected with *Rhizopus microsporus*; and a consistent breath signature of α-guaiene and alloaromadendrene in the breath of mice infected with *Rhizopus arrhizus* var. *delemar* (FIGS. 3A-I).

Figure 4:
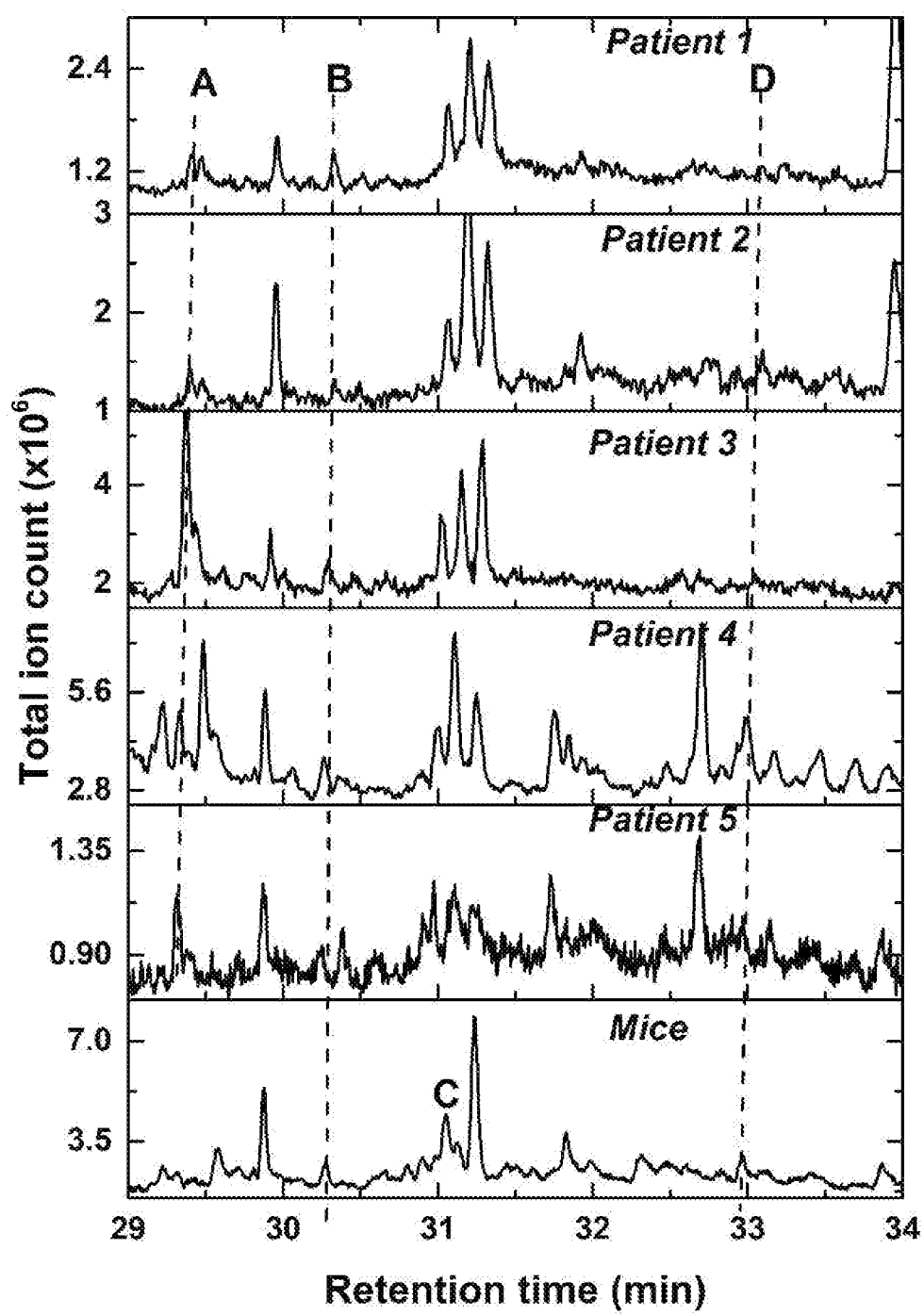
FIG. 4. Alignment of human (top 5 panels) and murine (bottom panel) breath samples in patients and mice with invasive *Rhizopus microsporus* infection—(A) is 1H-Indene,2,3,3a,4-tetrahydro-3,3a,6-trimethyl-1-(1-methylethyl)-, (B) cedrene, (C) selina-5,11-diene, and (D) cedranoxide, 8,14-
Figure 5A:
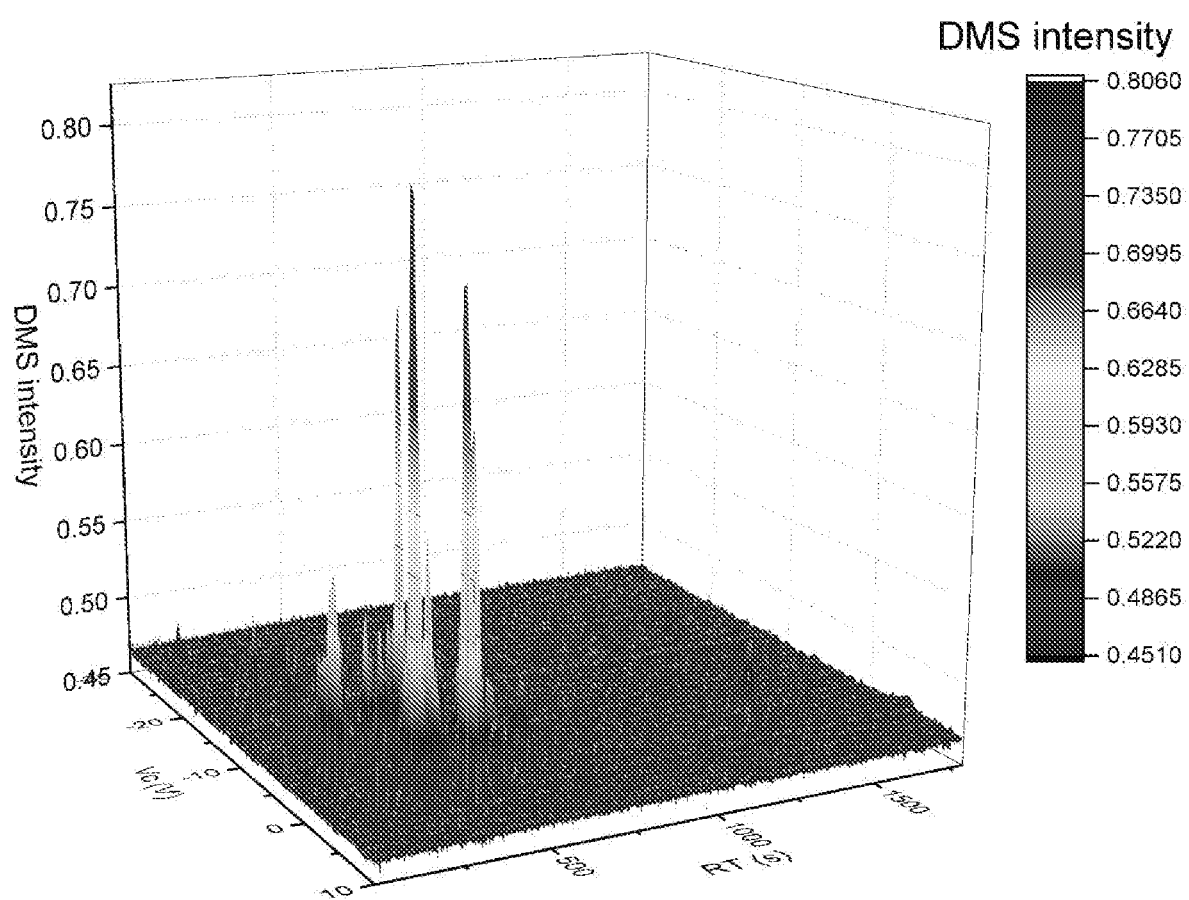
FIGS. 5A-B. GC-DMS analysis of a breath sample from a patient with proven *Rhizopus microsporus* infection, with sesquiterpene metabolites eluting at Vc+3.6 at around 1280 and 1330 seconds. 5A, global GC-DMS of breath sample; 5B, GC-DMS analysis at Vc=+3.6.
Figure 5B:
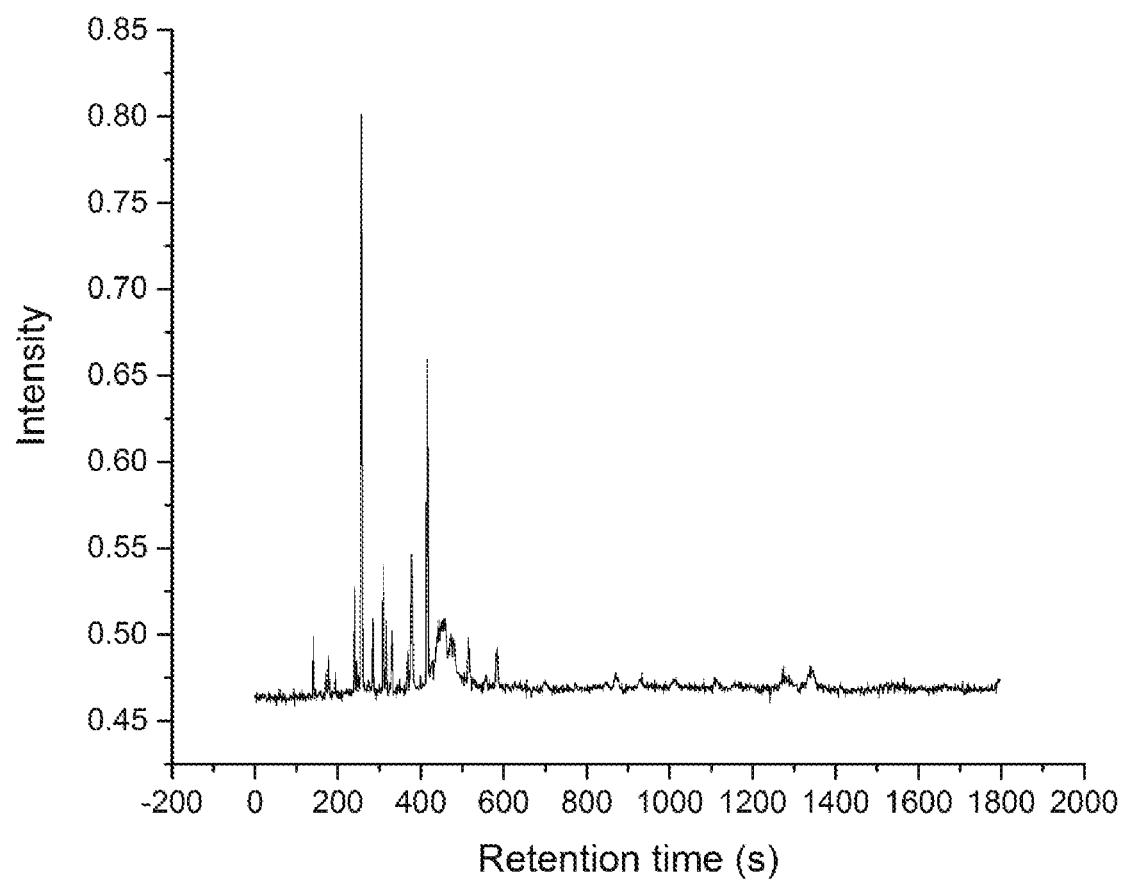

Five patients with proven invasive mucormycosis caused by *Rhizopus microsporus* had a consistent breath signature of cedrene, cedranoxide, 8, 14-, and 1H-Indene, 2,3,3a,4-tetrahydro-3,3a,6-trimethyl-1-(1-methylethyl)-, with some metabolite overlap with those found in the breath of mice infected with *Rhizopus microsporus* (FIG. 4); these breath metabolites were also discernible using GC-DMS (FIGS. 5A-B).

Figure 6A:
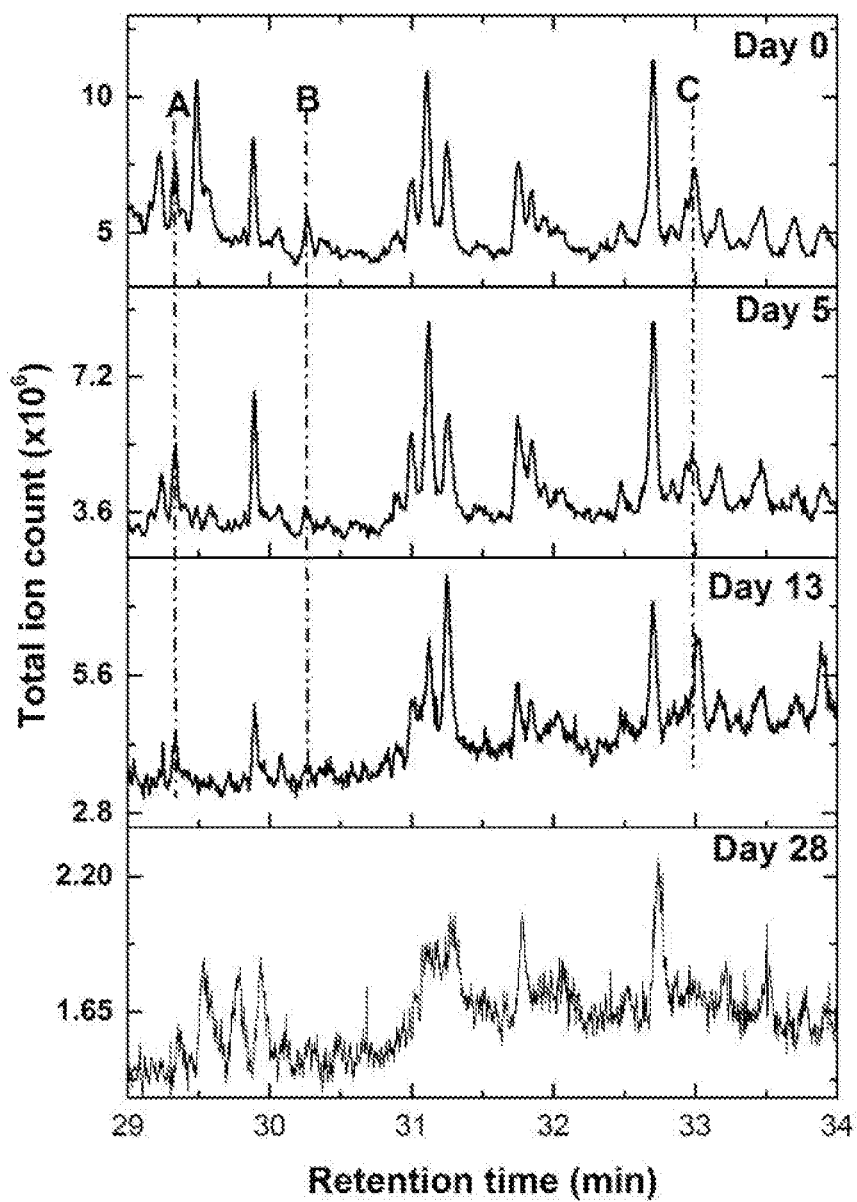
FIG. 6A. Alignment of sequential GC-MS analysis of breath samples from a patient with proven *Rhizopus microsporus* infection, from day 0 (start of isavuconazole antifungal therapy), with gradual attenuation and disappearance of these three sesquiterpene metabolites (A) 1H-Indene, 2,3,3a,4-tetrahydro-3,3a,6-trimethyl-1-(1-methylethyl)-, (B) cedrene, (C) cedranoxide, 8,14- over the 28-day treatment course.
Figure 6B:
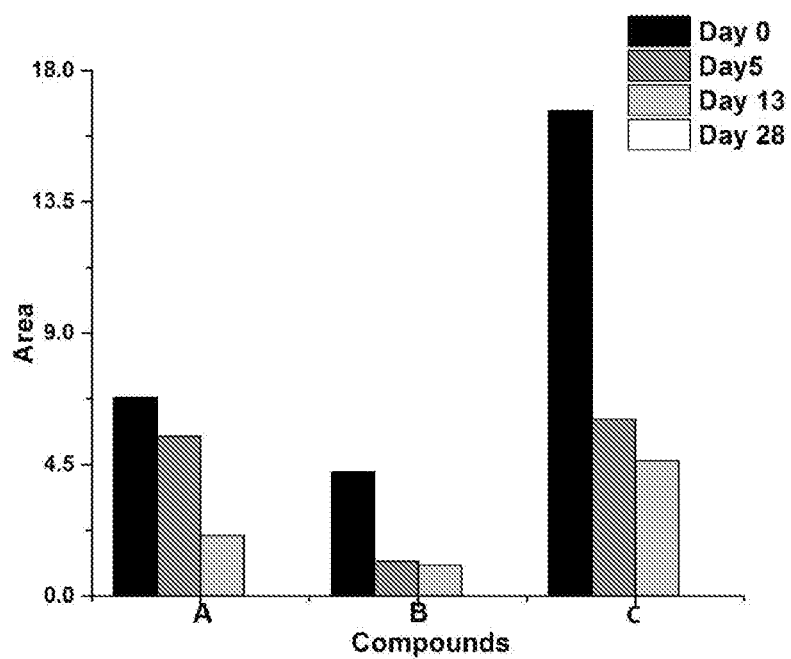
FIG. 6B. Bar graph illustrating gradual attenuation and disappearance of these three sesquiterpene metabolites (A) 1H-Indene, 2,3,3a,4-tetrahydro-3,3a,6-trimethyl-1-(1-methylethyl)-, (B) cedrene, (C) cedranoxide, 8,14- over the 28-day treatment course.

This breath signature declined gradually with antifungal therapy, eventually disappearing from the breath in one patient with *R. microsporus* infection who provided sequential breath samples (FIG. 6).

The most common Mucorales pathogenic to humans have distinct volatile secondary metabolite signatures that distinguish these fungal species from *Aspergillus* species. These volatile metabolite signatures are useful in the noninvasive, breath-based identification of patients with invasive mucormycosis, the differentiation of these patients from those with invasive aspergillosis and other infections, and potentially the monitoring of treatment response in patients with these infections.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing a subject with mucormycosis, the method comprising:
    obtaining a sample comprising breath of a subject or suspected of comprising a Mucorales species fungi isolated from a subject;
    detecting the presence in the sample of volatile organic compounds (VOCs) produced by the Mucorales species in a sample comprising breath from the subject or headspace from a culture suspected of comprising Mucorales isolated from the subject, wherein the VOCs are cedrene 8,14-, cedrene, and 1H-Indene, 2,3,3a,4-tetrahydro-3,3a,6-trimethyl-1-(1-methylethyl)-;
    and
    diagnosing a subject as having mucormycosis when the VOCs are present in the sample.

2. The method of claim 1, comprising detecting the presence in a sample comprising headspace from a culture of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene, wherein:
    the presence of one, two, three or more of 1H-Indene, 2,3,3a,4-tetrahydro-3,3a,6-trimethyl-1-(1-methyl-ethyl)-, longipinene, cedrene, aromandendrene, alloaromadendrene, cubebol, and aciphyllene indicates a diagnosis of *Rhizopus arrhizus* var. *arrhizus*;

the presence of one, two, three or more of 1H-Indene, 2,3,3a,4-tetrahydro-3,3a,6-trimethyl-1-(1-methylethyl)-, isoledene, daucene, isocomene, isocaryophyllene, humulene, and isodaucene indicates a diagnosis of *Rhizopus arrhizus* var. *delemar*; and the presence of one, two, three or more of alloaromadendrene, cubebene, cyperene, and α-bisabolene indicates a diagnosis of *Rhizopus* microsporus.

3. The method of claim 1, comprising detecting the presence, in a sample breath from a subject suspected of being infected with Mucorales fungi, a level of one, two, three, four or more of Cedrene; cedranoxide, 8, 14-; 1H-Indene,2,3,3a,4-tetrahydro-3,3a,6-trimethyl-1-(1-methylethyl)-; Longifolene; 2H-3,9a-Methano-1-benzoxepin; octahydro-2,2,5a,9-tetramethyl-,[3R-(3a,5aa,9a,9aa)]-; cis-(−)2,4a,5,6,9a-Hexahydro-3,5,5,9-tetramethyl(1H)benzocycloheptene; selina-5,11-diene; or α-guaiene; alloaromadendrene, wherein:

the presence of one, two, three, or more of longifolene; 2H-3,9a-Methano-1-benzoxepin; octahydro-2,2,5a,9-tetramethyl-,[3R-(3a,5aa,9a,9aa)]-; and cis-(−)2,4a,5,6,9a-Hexahydro-3,5,5,9-tetramethyl (1H)benzocycloheptene indicates the presence of *Rhizopus arrhizus* var. *arrhizus*;

the presence of one, two, or all three of cedrene; selina-5,11-diene; and cedranoxide, 8, 14-indicates the presence of *Rhizopus microsporus*; and the presence of α-guaiene and alloaromadendrene indicates the presence of *Rhizopus arrhizus* var. *delemar*.

4. The method of claim 1, comprising detecting the presence in a sample comprising breath from a subject suspected of being infected with Mucorales fungi, the presence of one, two, or all three of cedrene; cedranoxide, 8, 14-; and 1H-Indene, 2,3,3a,4-tetrahydro-3,3a,6-trimethyl-1-(1-methylethyl)-, and diagnosing the patient with a Mucorales fungal infection.

5. The method of claim 4, comprising detecting the presence of one, two, three, or all four of 1H-Indene, 2,3,3a,4-tetrahydro-3,3a,6-trimethyl-1-(1-methylethyl)-; cedrene; selina-5,11-diene, and cedranoxide, 8,14-, and diagnosing the patient with a Mucorales fungal infection.

6. The method of claim 4, wherein the Mucorales fungal infection is an infection with a *Rhizopus* species fungus.

7. The method of claim 2, further comprising selecting and optionally administering an antifungal treatment for mucormycosis to a subject, wherein one, two, three, or more of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene was detected in the headspace from a culture from the subject.

8. The method of claim 4, further comprising selecting and optionally administering an antifungal treatment for mucormycosis to a subject who has cedrene; cedranoxide, 8, 14-; and 1H-Indene, 2,3,3a,4-tetrahydro-3,3a,6-trimethyl-1-(1-methylethyl)- in their breath.

9. The method of claim 7, wherein the treatment comprises administration of one or more doses of one or more antifungal compounds.

10. The method of claim 8, wherein the treatment comprises administration of one or more doses of one or more antifungal compounds.

11. The method of claim 1, comprising:
determining a first level of one, two, three, or more volatile organic compounds (VOCs) produced by a mucormycosis species in a sample comprising breath from the subject or headspace from a culture suspected of comprising Mucorales fungi isolated from the subject, wherein the VOCs are cedrene 8,14-, cedrene, and 1H-Indene, 2,3,3a,4-tetrahydro-3,3a,6-trimethyl-1-(1-methylethyl)-, and optionally cedranoxide 8-14-, in the subject;

diagnosing a subject as having mucormycosis when the VOCs are present in the sample, administering a treatment for mucormycosis to the subject;

determining a second level of the VOCs in a sample obtained after administration of the treatment to the subject; and comparing the first and second levels of VOCs, wherein a decrease in the VOCs indicates that the treatment has been effective in treating the mucormycosis in the subject, and an increase or no change indicates that the treatment has not been effective in treating the mucormycosis in the subject.

12. The method of claim 11, wherein the treatment comprises administration of one or more doses of one or more antifungal compounds.

13. A method of identifying a candidate compound for the treatment of mucormycosis, the method comprising:
providing a test culture comprising one or more Mucorales species;

detecting a baseline level of fungal VOCs in the headspace of the culture in the absence of the test compound, wherein the VOCs are cedrene 8,14- and 1H-Indene, 2,3,3a,4-tetrahydro-3,3a,6-trimethyl-1-(1-methylethyl)-, and optionally cedranoxide 8-14-, in the subject;

contacting the test culture with a test compound;

determining a second level of the VOCs in a the test culture;

comparing the second level of VOCs to the baseline level; and identifying a test compound that decreases levels of fungal VOCs in the test culture as a candidate compound for the treatment of mucormycosis.

14. A method of detecting the presence of a mucormycosis infection in a culture, the method comprising:
obtaining a sample comprising gas from the headspace of the culture;

determining the presence of 1H-Indene, 2,3,3a,4-tetrahydro-3,3a,6-trimethyl-1-(1-methylethyl)-, aciphyllene, alloaromadendrene, cedrene, Cubebene, cubebol, Cyperene, Daucene, Humulene, Isocaryophyllene, Isocomene, Isodaucene, Isoledene, Longipinene, and α-bisabolene, wherein:

the presence of one, two, three or more of 1H-Indene, 2,3,3a,4-tetrahydro-3,3a,6-trimethyl-1-(1-methylethyl)-, longipinene, cedrene, aromandendrene, alloaromadendrene, cubebol, and aciphyllene indicates the presence of *Rhizopus arrhizus* var. *arrhizus* in the culture;

the presence of one, two, three or more of 1H-Indene, 2,3,3a,4-tetrahydro-3,3a,6-trimethyl-1-(1-methylethyl)-, isoledene, daucene, isocomene, isocaryophyllene, humulene, and isodaucene indicates the presence of *Rhizopus arrhizus* var. *delemar* in the culture; and the presence of one, two, three or more of alloaromadendrene, cubebene, cyperene, and α-bisabolene indicates the presence of *Rhizopus microsporus* in the culture.

15. The method of claim 1, wherein determining the presence of a VOC comprises assaying the sample to detect the presence the VOC.

16. The method of claim 15, wherein assaying the sample to detect the presence the VOC comprises using a gas chromatography (GC) or spectrometry method.

17. The method of claim 16, wherein the spectrophotometry method is mobility spectrometry (IMS) or differential mobility spectrometry (DMS).

18. The method of claim 1, wherein the subject is a human.

19. The method of claim 1, wherein the antifungal compound is an amphotericin B formulation; an azole antifungal compound; or an echinocandin antifungal compound.

* * * * *